(12) United States Patent
Fontanel et al.

(10) Patent No.: US 11,707,225 B2
(45) Date of Patent: Jul. 25, 2023

(54) BIO-SENSING BASED MONITORING OF HEALTH

(71) Applicant: Samsung Electronics Company, Ltd., Suwon-si (KR)

(72) Inventors: Fannie Fontanel, Sunnyvale, CA (US); Jawahar Jain, Los Altos, CA (US); Sajid Sadi, Mountain View, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 653 days.

(21) Appl. No.: 15/965,542

(22) Filed: Apr. 27, 2018

(65) Prior Publication Data
US 2019/0328316 A1   Oct. 31, 2019

(51) Int. Cl.
*A61B 5/00*   (2006.01)
*G06T 7/70*   (2017.01)
(Continued)

(52) U.S. Cl.
CPC ............ *A61B 5/486* (2013.01); *A61B 5/0077* (2013.01); *A61B 5/0245* (2013.01); *A61B 5/02405* (2013.01); *A61B 5/02416* (2013.01); *A61B 5/02438* (2013.01); *A61B 5/1072* (2013.01); *A61B 5/1075* (2013.01); *A61B 5/1079* (2013.01); *A61B 5/1118* (2013.01); *A61B 5/165* (2013.01); *A61B 5/4884* (2013.01);
(Continued)

(58) Field of Classification Search
CPC ..... A61B 5/486; A61B 5/1079; A61B 5/4884; A61B 5/0245; A61B 5/02416; A61B 5/02438; A61B 5/02405; A61B 5/7275; A61B 5/1075; A61B 5/1072; A61B 5/1118; A61B 5/165; A61B 5/0077; A61B 5/7246; G06T 7/70; G06T 7/13; G06T 7/60; G06T 2207/30196; G06T 2207/30004; G16H 10/60; G16H 50/20; G16H 50/70; G16H 30/40; G16H 40/67; G06F 3/04842

See application file for complete search history.

(56) References Cited

U.S. PATENT DOCUMENTS

2008/0146961 A1   6/2008  Okura
2011/0144145 A1   6/2011  Tollefson
(Continued)

FOREIGN PATENT DOCUMENTS

WO   WO2017065694 A1 *  4/2017  ........... A61B 5/0478

OTHER PUBLICATIONS

Hendrawan et al. 2012 Internat. J. Psychophysiology 84:277-283 (Year: 2012).*
(Continued)

*Primary Examiner* — Keith M Raymond
*Assistant Examiner* — Patrick M Mehl

(57) ABSTRACT

In one embodiment, a health-monitoring system may access a waist-hip measurement of a user. The system may determine one or more stress-related parameters of the user using one or more computing devices. The system may determine one or more correlations between the waist-hip measurement and the one or more stress-related parameters of the user. The system may provide feedback to the user based on one or more of the one or more stress-related parameters or the determined correlations between the waist-hip measurement and the one or more stress-related parameters.

44 Claims, 22 Drawing Sheets

(51) Int. Cl.
| | |
|---|---|
| G06T 7/13 | (2017.01) |
| A61B 5/107 | (2006.01) |
| A61B 5/0245 | (2006.01) |
| A61B 5/024 | (2006.01) |
| A61B 5/11 | (2006.01) |
| A61B 5/16 | (2006.01) |
| G16H 10/60 | (2018.01) |
| G16H 50/20 | (2018.01) |
| G06T 7/60 | (2017.01) |
| G06F 3/04842 | (2022.01) |

(52) U.S. Cl.
CPC .......... *A61B 5/7246* (2013.01); *A61B 5/7275* (2013.01); *G06T 7/13* (2017.01); *G06T 7/60* (2013.01); *G06T 7/70* (2017.01); *G16H 10/60* (2018.01); *G16H 50/20* (2018.01); *A61B 2562/0219* (2013.01); *G06F 3/04842* (2013.01); *G06T 2207/30196* (2013.01)

(56) References Cited

U.S. PATENT DOCUMENTS

| | | |
|---|---|---|
| 2011/0251096 A1 | 10/2011 | Southern |
| 2012/0178118 A1 | 7/2012 | Pi |
| 2012/0283530 A1 | 11/2012 | Maynard |
| 2014/0031700 A1 | 1/2014 | Ferrantelli |
| 2014/0046189 A1 | 2/2014 | Jain |
| 2014/0089836 A1 | 3/2014 | Damani |
| 2014/0147850 A1 | 5/2014 | Urdea |
| 2014/0257708 A1 | 9/2014 | Bilello |
| 2014/0348417 A1* | 11/2014 | Moore ................ A61B 5/1075 382/154 |
| 2015/0112452 A1* | 4/2015 | He ........................ A61B 5/113 700/11 |
| 2015/0119417 A1 | 4/2015 | Tollefson |
| 2015/0164399 A1 | 6/2015 | Beg |
| 2015/0174362 A1 | 6/2015 | Panova |
| 2015/0223730 A1 | 8/2015 | Ferrantelli |
| 2015/0317813 A1* | 11/2015 | Vendrow ................ G06T 11/60 345/634 |
| 2016/0088284 A1 | 3/2016 | Sareen |
| 2016/0247017 A1* | 8/2016 | Sareen ................ A61B 5/0064 |
| 2016/0342757 A1 | 11/2016 | Bilello |
| 2017/0071523 A1 | 3/2017 | Jain |
| 2017/0071551 A1* | 3/2017 | Jain ................ A61B 5/02438 |
| 2017/0079572 A1 | 3/2017 | Jang |
| 2017/0138962 A1 | 5/2017 | Southern |
| 2017/0161441 A1 | 6/2017 | Bilello |
| 2017/0249437 A1 | 8/2017 | Jain |
| 2017/0249438 A1 | 8/2017 | Jain |
| 2017/0296874 A1* | 10/2017 | Zamir ................ A61B 5/7271 |
| 2018/0001184 A1* | 1/2018 | Tran ........................ H04W 4/38 |

OTHER PUBLICATIONS

Steptoe et al. 2005 Internat. J. Obesity 29:1329-1337 (Year: 2005).*
Hernandez-Vela 2015 Ph.D. Thesis University of Barcelona, Department of Mathematics, 148 pages (Year: 2015).*
Schubert et al. 2009 Biological Psychology 80:325-332 (Year: 2009).*
Sun et al. 2012 MOBICASE 2010 LNICST 76:282-301 (Year: 2012).*
Garbarino et al. 2014 IEEE 2014 4th International Conference on Wireless Mobile Communication and Healthcare—Transforming Healthcare Through Innovations in Mobile and Wireless Technologies (MOBIHEALTH), Athens, Greece, 2014, pp. 39-42, doi: 10.1109/MOBIHEALTH.2014.7015904 (Year: 2014).*
Gjoreski et al. 2017 J. Biomed. Informatics 73:159-170 (Year: 2017).*
Burke et al. 2011 Obesity 19:338-344 (Year: 2011).*
Gluck et al. 2004 Ann. N.Y. Acad. Sci. 1032: 202-207 (Year: 2004).*
Epel et al., "Stress and Body Shape: Stress-Induced Cortisol Secretion is Consistently Greater among Women with Central Fat," America Psychosomatic Society, Feb. 15, 2000.
Arie G. Nieuwenhiuzen, "The hypothalamic-pituitary-adrenal-axis in the regulation of energy balance," Physiology & Behavior 94, Dec. 17, 2007.
Johan Vester, "Estimating the Height of an Unknown Object in a 2D Image," KTH Computer Science and Communication, 2012.
ITunes Review, Hip Waist Ratio by Egate IT Solutions Pvt Ltd, 2017.
Appbrain, WHR—Waist to HipRation, by Designwareapp, 2017.

* cited by examiner

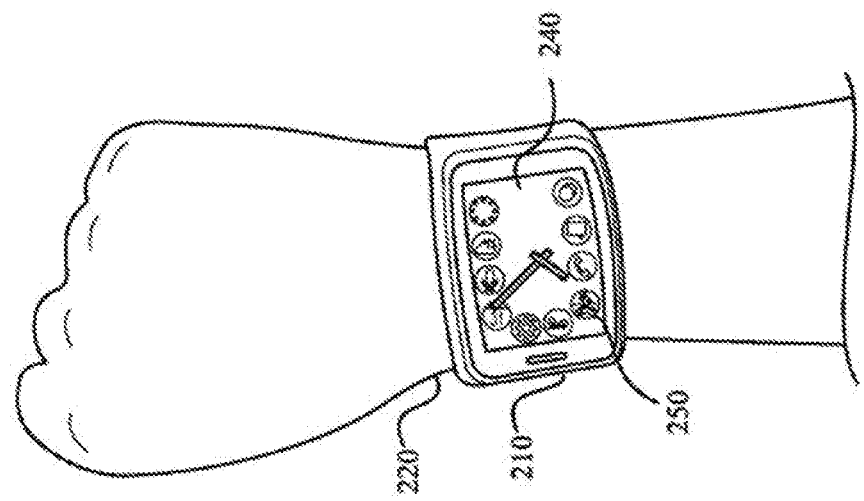
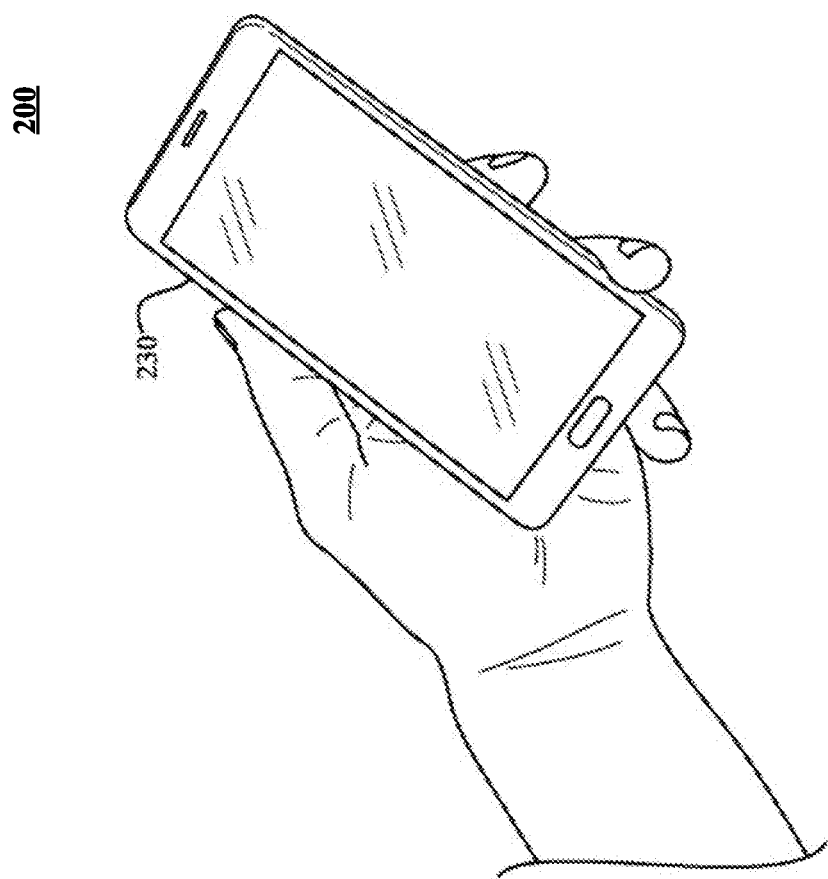
*FIG. 2*

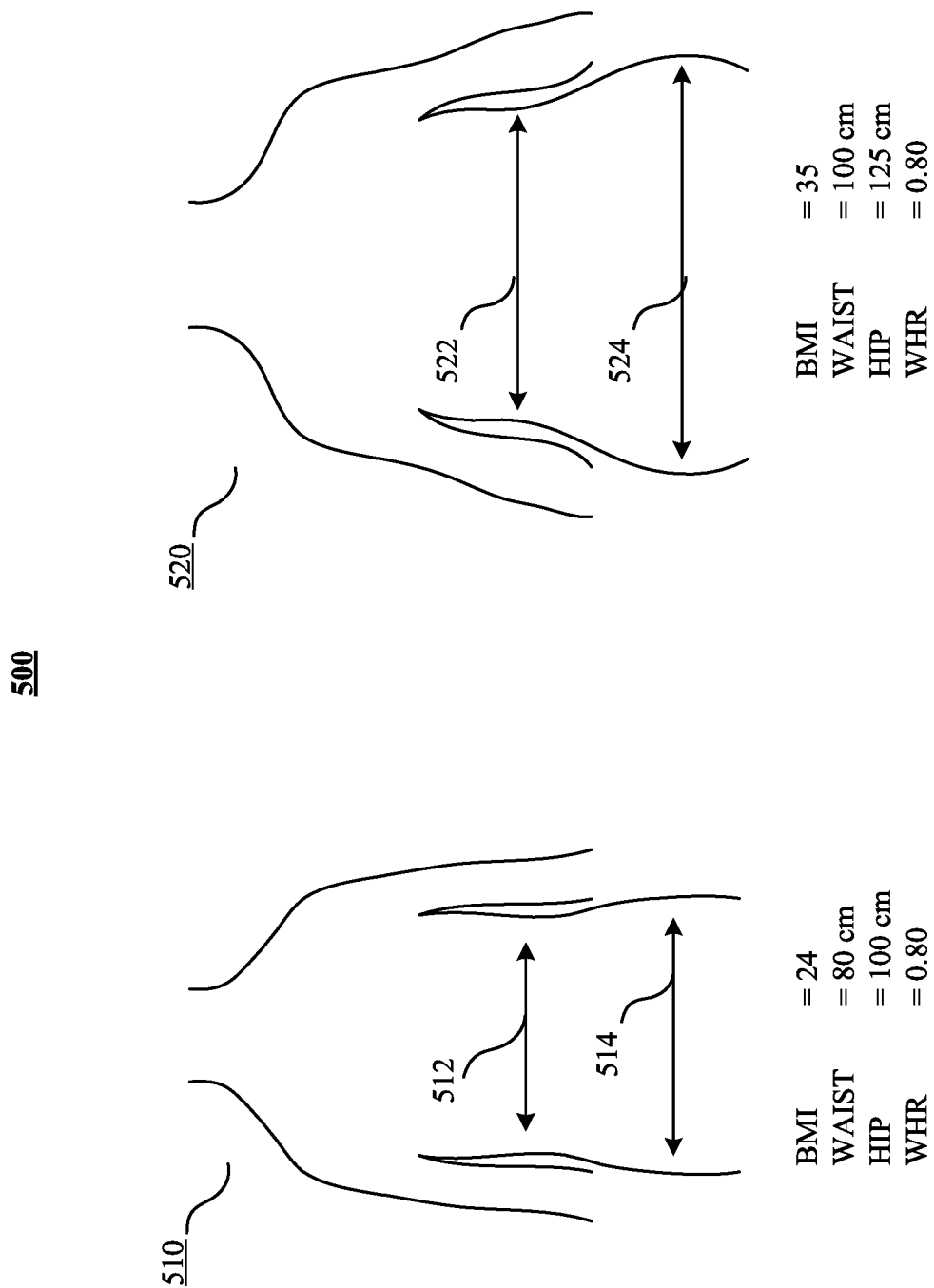

BIO-SENSING BASED MONITORING OF HEALTH

TECHNICAL FIELD

This disclosure generally relates to monitoring health and providing feedback to a user.

BACKGROUND

It may be important to determine indicators or markers for controllable anthropomorphic measurements, for example, but not limited to, increasing belly fat. These measurements may enable not only a better titration or adjustment of treatment but also allow users to undertake healthier lifestyles. Quality of Life (QOL), depression, and measures of neurological disturbances may be different perspectives of an increasing VAT (Visceral Adipose Tissues). QOL may be the general well-being of individuals and societies, outlining negative and positive features of life. An assessment of Health-Related Quality of Life (HRQOL) may be an effective evaluation of QOL and the relationship with health.

Among the large number of markers or indicators for cardiovascular disease, the waist-to-hip ratio (WHR) may be the simplest and most accurate. Furthermore, the WHR may be associated with stress conditions like stress resilience. A higher WHR may be associated with a higher cortisol secretion which in turn may lead to a greater waist fat formation and higher WHR. A greater waist fat formation or a higher WHR may also be a cause for poor stress resilience. The relationship between the waist fat formation or the WHR and the stress conditions or cortisol secretion is bi-directional. In many cases, WHR is one of the most important markers for metabolic health.

BRIEF DESCRIPTION OF THE DRAWINGS

FIG. 2 illustrates an example health monitoring system including systems and devices according to particular embodiments.

FIGS. 5A-5B illustrate examples of body mass index (BMI) and WHR.

DESCRIPTION OF EXAMPLE EMBODIMENTS

Figure 1:
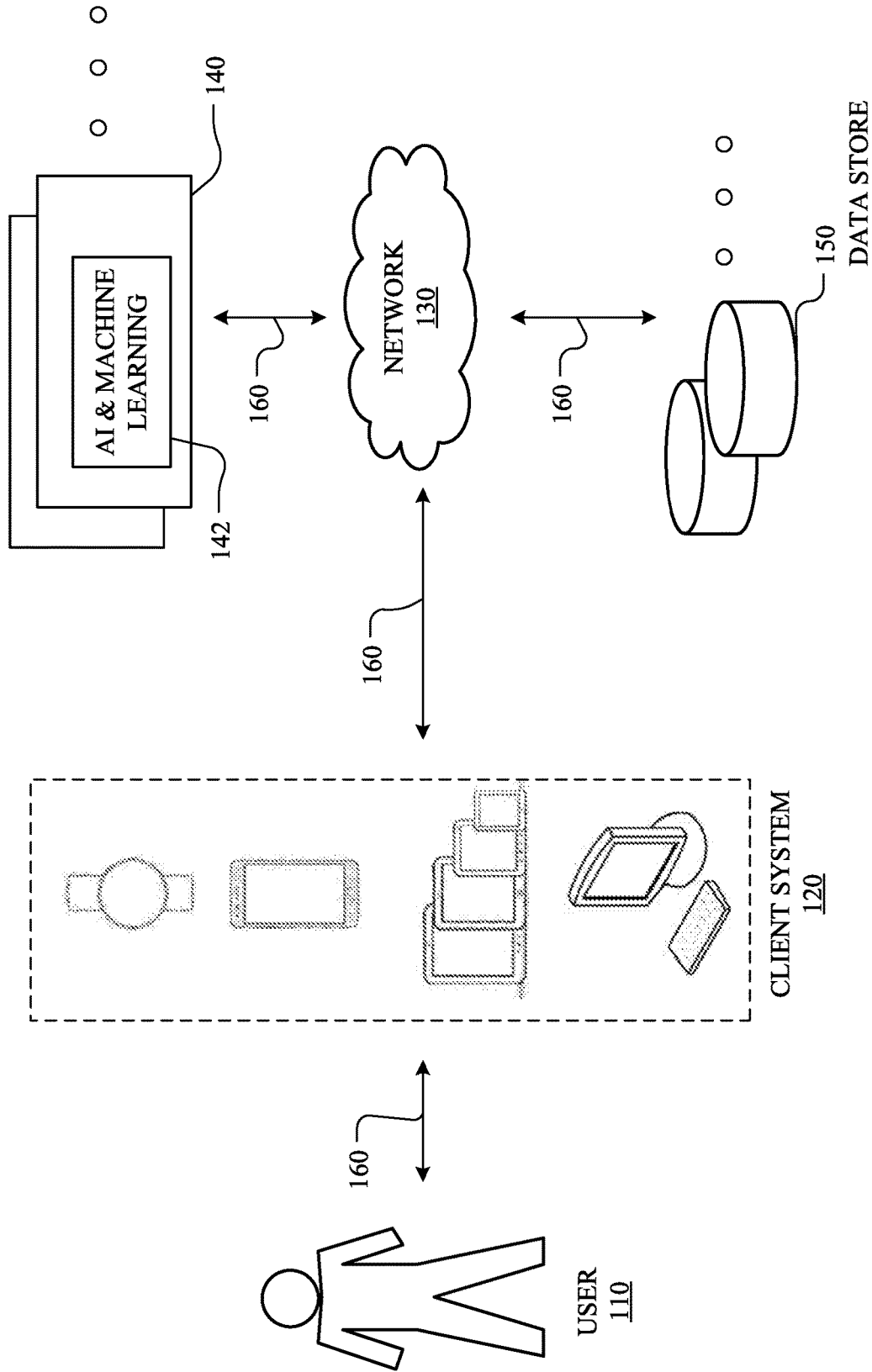
FIG. 1 illustrates an example network environment for particular embodiments of a health monitoring system.

FIG. 1 illustrates an example network environment 100 for particular embodiments of a health monitoring system. Network environment 100 includes a user 110, a client system 120, a network 130, one or more servers 140, and one or more data stores 150. User 110, client system 120, servers 140, and data stores 150 may be connected to each other by network 130 via links 160. Although FIG. 1 illustrates a particular arrangement of user 110, client system 120, network 130, servers 140, and data stores 150, this disclosure contemplates any suitable arrangement of user 110, client system 120, network 130, servers 140, and data stores 150. As an example and not by way of limitation, two or more of client systems 120, servers 140, and data stores 150 may be connected to each other directly, bypassing network 130. As another example, two or more of client systems 120, servers 140, and data stores 150 may be physically or logically co-located with each other in whole or in part. Moreover, although FIG. 1 illustrates a particular number of user 110, client system 120, network 130, servers 140, and data stores 150, this disclosure contemplates any suitable number of user 110, client system 120, network 130, servers 140, and data stores 150. As an example and not by way of limitation, network environment 100 may include multiple users 110, client systems 120, networks 130, servers 140, and data stores 150.

In particular embodiments, user 110 may be an individual (e.g., human user), an entity (e.g., an enterprise, business, or third-party application), or a group (e.g., of individuals or entities) that interacts or communicates with client system 120. In particular embodiments, client system 120 may be any suitable computing device, such as, for example, a wearable computing device, a mobile computing device, a smartphone, a smartwatch, a cellular telephone, a tablet computer, a laptop computer, a personal computer, an augmented/virtual reality device, or any combination thereof. User 110 may interact with one or more of these devices. In addition, these devices may communicate with each other via network 130, directly (e.g., by non-network connections), by any other suitable methods, or any combination thereof. As an example and not by way of limitation, the devices of client system 120 may communicate with network 130 via a wireless communications protocol, such as Wi-Fi or BLUETOOTH. In particular embodiments, client system 120 may include a web browser, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. A user at client system 120 may enter a Uniform Resource Locator (URL) or other address directing the web browser to a particular server (such as server 140), and the web browser may generate a Hyper Text Transfer Protocol (HTTP) request and communicate the HTTP request to server. The server may accept the HTTP request and communicate to client system 120 one or more Hyper Text Markup Language (HTML) files responsive to the HTTP request. Client system 120 may render a webpage based on the HTML files from the server for presentation to the user. This disclosure contemplates any suitable webpage files. As an example and not by way of limitation, webpages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a webpage encompasses one or more corresponding webpage files (which a browser may use to render the webpage) and vice versa, where appropriate.

In particular embodiments, network 130 may be any suitable network. As an example and not by way of limitation, one or more portions of network 130 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 130 may include one or more networks.

In particular embodiments, links 160 may connect client system 120, servers 140, and data stores 150 to network 130 or to each other. This disclosure contemplates any suitable links 160. In particular embodiments, one or more links 160 include one or more wireline (such as for example Digital Subscriber Line (DSL) or Data Over Cable Service Interface Specification (DOCSIS)), wireless (such as for example Wi-Fi or Worldwide Interoperability for Microwave Access (WiMAX)), or optical (such as for example Synchronous Optical Network (SONET) or Synchronous Digital Hierarchy (SDH)) links. In particular embodiments, one or more links 160 each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link 160, or a combination of two or more such links 160. Links 160 need not necessarily be the same throughout network environment 100. One or more first links 160 may differ in one or more respects from one or more second links 160.

In particular embodiments, servers 140 may be any suitable servers. Each server 140 may be a unitary server or a distributed server spanning multiple computers or multiple datacenters. Servers 140 may be of various types, such as, for example and not by way of limitation, web server, file server, application server, exchange server, database server, proxy server, another server suitable for performing functions or processes described herein, or any combination thereof. In particular embodiments, each server 140 may include hardware, software, or embedded logic components or a combination of two or more such components for carrying out the appropriate functionalities implemented or supported by server 140. In particular embodiments, servers 140 may include one or more artificial intelligence (AI) and machine learning (ML) algorithms 142. In particular embodiments, one or more artificial intelligence (AI) and machine learning (ML) algorithms may be implemented in client system 120. In particular embodiments, the artificial intelligence (AI) and machine learning (ML) algorithms may be deep learning algorithms. In particular embodiments, the data store 150 may include a data base including a number of meal pictures. In particular embodiments, the artificial intelligence (AI) and machine learning (ML) algorithms 142 may analyze data stored in data stores 150 and provide analyzing results to user 110 through client system 120.

In particular embodiments, data stores 150 may be any suitable data stores. Data stores 150 may be used to store various types of information. In particular embodiments, the information stored in data stores 150 may be organized according to specific data structures. In particular embodiments, each data store 150 may be a relational, columnar, correlation, or other suitable database. Data store 150 may include networked storage such as cloud storage or other network accessible storage. Additionally or alternatively, data store 150 may include local storage within or directly attached to any of the devices of client system 120, such as solid state drives ("SSDs") or hard disk drives ("HDDs"). The network environment illustrated in FIG. 1 is for example only and the network environments are not limited thereto. Although this disclosure describes or illustrates particular types of components and uses of these components of network environment 100, this disclosure contemplates any suitable types of components, any suitable network topology (e.g., including a standalone-device topology), and any suitable uses for these components of network environment 100.

FIG. 2 illustrates an example health monitoring system 200 including systems and devices according to particular embodiments. In particular embodiments, as shown in FIG. 2, health monitoring system 200 may include a health monitoring device 210 (e.g., positioned on user wrist 220) and a mobile electronic device 230. Health monitoring device 210 may be a wearable electronic device (e.g., a smartwatch, a device of client system 120, etc.) that can be worn on a portion of the user's body, such as an arm, wrist, finger, leg, ankle, toe, torso, neck, head, any other suitable portion of the body, or any combination thereof. Health monitoring device 210 may include a user interface 240, which may include a watch-like user interface in addition to one or more applications 250 (e.g., a weather application, an exercise application, a chat application, etc.). In particular embodiments, health monitoring device 210 may be a health monitoring patch adhered to a portion of the user's body, such as an arm, wrist, leg, ankle, torso, neck, head, any other suitable portion of the body, or any combination thereof. In particular embodiments, health monitoring device 210 may be a mobile device such as mobile electronic device 230.

In particular embodiments, health monitoring device 210 may connect to mobile electronic device 230 directly or via network 130, which may facilitate interaction between and/or transfer of data between health monitoring device 210 and mobile electronic device 230. In particular embodiments, mobile electronic device 230 may be a smartphone-like device. Health monitoring device 210 and mobile electronic device 230 may be connected to network 130, servers 140, data stores 150, or any combination thereof. Data (e.g., heart rate, stress level, sleep time, emotional state, etc.) may be stored on health monitoring device 210, mobile electronic device 230, other client systems 120, data stores 150, other suitable databases, or any combination thereof. In addition, the processing of the data and computations of particular algorithms (as discussed below) may be performed by health monitoring device 210, mobile electronic device 230, servers 140, any other client system 120, other suitable devices/systems, or any combination thereof. In particular embodiments, the processing of the data and computations of particular algorithms may be performed by accessing user data, frame of reference/baseline data, medical data, other relevant data, or any combination thereof, from data stores 150 via network 130. Although this disclosure describes a health monitoring system having particular components, this disclosure contemplates a health monitoring system with any suitable components.

Figure 3:
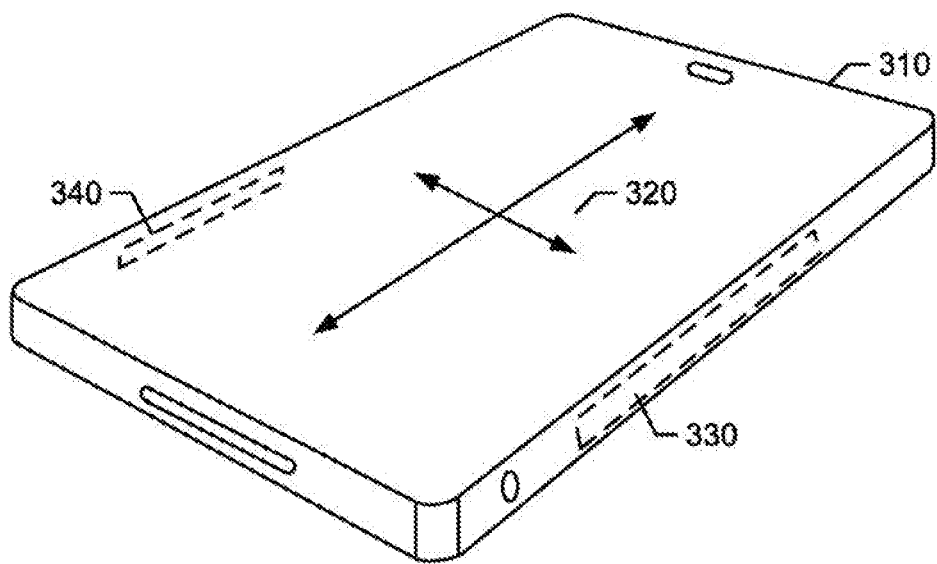
FIG. 3 illustrates an example mobile client system.

FIG. 3 illustrates an example mobile client system 300 (e.g., mobile electronic device 230, a client system 120). This disclosure contemplates mobile client system 300 taking any suitable physical form. In particular embodiments, mobile client system 300 may be a computing system as described below. As an example and not by way of limitation, mobile client system 300 may be a single-board computer system (SBC) (such as, for example, a computer-on-module (COM), a system-on-module (SOM), or a system-in-package (SiP)), a laptop or notebook computer system, a mobile telephone, a smartphone, a personal digital assistant (PDA), a tablet computer system, or a combination of two or more of these. In particular embodiments, mobile client system 300 may have a display screen 310 and a touch sensor 320 as an input component. In particular embodiments, mobile client system may have the display screen 310 and the touch sensor 320 integrated in a touch screen. In the example of FIG. 3, touch sensor 320 is incorporated on a front surface (e.g., display screen 310) of mobile client system 300. Touch sensor 320 may detect the presence and location of a touch (e.g., from one or more fingers of a user) or the proximity of an object (e.g., a stylus). In the case of capacitive touch sensors, there may be two types of electrodes: transmitting and receiving. These electrodes may be connected to a controller designed to drive the transmitting electrodes with electrical pulses and measure the changes in capacitance from the receiving electrodes caused by a touch or proximity input. In particular embodiments, a user may be presented with a user interface ("UI") of one or more applications (e.g., mobile applications) on screen display 310 of mobile client system 300, and the user may interact with the UI of each of the applications via touch sensor 320.

In the example of FIG. 3, one or more antennae 330, 340 may be incorporated into one or more sides of mobile client system 300. Antennae 330, 340 are components that convert electric current into radio waves, and vice versa. In particular embodiments, a communication component coupled to antennae 330, 340 of mobile client system 300 may be configured to determine location data based on global positioning system (GPS) signals, cellular triangulation, wireless hotspots, or any suitable methods for determining location data.

One advantage of particular embodiments of the health-monitoring system disclosed herein is the provision of services for diagnosis and/or treatment of various chronic diseases based on such devices. Another advantage of particular embodiments is providing feedback to a user so that the user can modulate her lifestyle to reduce disease or to improve quality of life. Particular embodiments also or alternatively provide doctors useful information for establishing a diagnosis or to otherwise assist clinical evaluation.

Figures 4A, 4B:
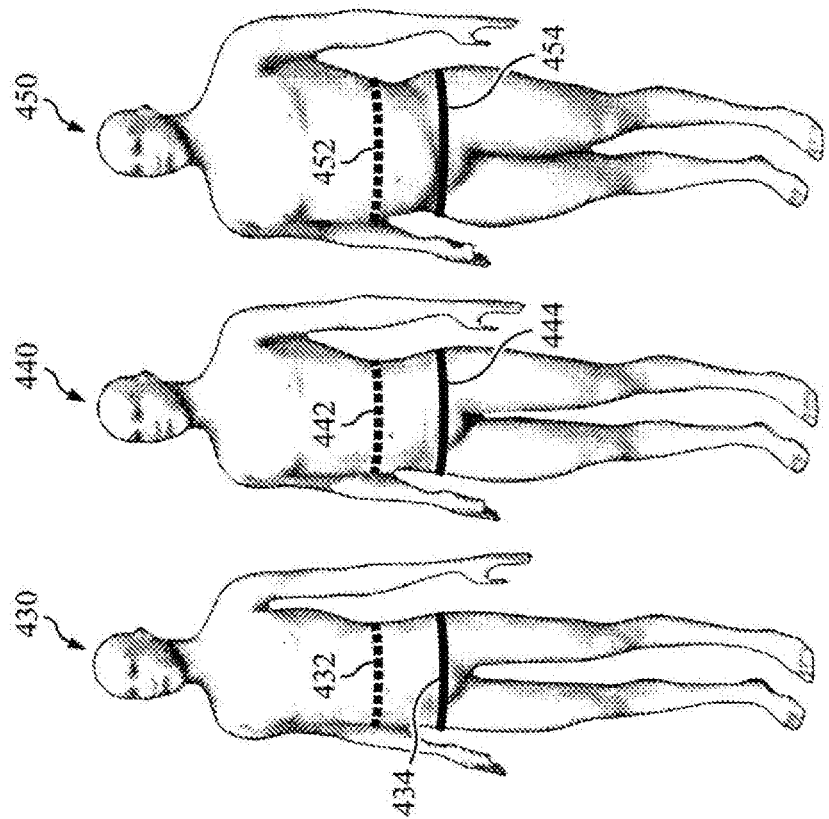
FIG. 4A illustrates two exemplary body shapes including the apple shape and the pear shape.
FIG. 4B illustrates three exemplary waist-to-hip ratios (WHRs) of users.

FIG. 4A illustrates two exemplary body shapes including the apple shape and the pear shape. The user 410 having an apple body shape may generally have a greater waist-to-hip ratio (WHR) than the user 420 having a pear body shape. In general, people having the apple body shape may face more health risks than people having the pear body shape. People having the apple body shape may have more weight around their waist while people having the pear body shape may have more weight around their hips. FIG. 4B illustrates three example wait-to-hip ratios (WHRs) of three users (430, 440, 450). WHR may be defined as a dimensionless ratio of waist size to hip size. WHR may be calculated as waist size (W) divided by hips size (H) so that WHR=W/H. The waist size may be a waist circumference or a waist length. The waist circumference may be measured along the circle around the user waist (e.g., 432, 442, 452 in FIG. 4B). The waist length may be measured in a particular way, for example, from one side to the other side of waist (e.g., 512 in FIG. 5A, 522 in FIG. 5B). Hips size may be the circumference including a person's hips or the length from one hip to another hip. Hip size may be measured along the circle around the user's hips (e.g., 434, 444, 454 in FIG. 4B). Hip length may be measured in a particular way, for example, from one side to the other side of hips (e.g., 514 in FIG. 5A, 524 in FIG. 5B).

As an example and not by way of limitation, a person with a 30 inches (76 cm) waist circumference and 38 inches (97 cm) hips circumference may have a waist-hip ratio of about 0.79. A waist-hip measurement may include measurements of all the parameters related to waist measurement, hip measurement, or both waist and hip measurement. As an example and not by way of limitation, the waist-hip measurement may include measurements of waist circumference, waist length, hips circumference, hips length, WHR, or other related parameters.

WHR may be used as an indicator or measure of health and the risk of developing serious health conditions. WHR may be correlated with fertility for which males and females may have different optimal values. WHR may be used as a measure of obesity, which in turn may be a possible indicator of other more serious health conditions.

In general, most individuals who qualify as obese may also have a WHR that indicates health-related danger. However, some people classified as "overweight" or "obese" may just be big in size, and their fat may be relatively distributed across their hips, legs, chest, and arms and less concentrated around their waist. Many individuals who qualify as "normal weight" may also carry too much of their body weight around their waist. The excess waist fat may be more dangerous than fat on legs or hips. Waist fat may tend to contain omega-six fatty acid such as linoleic acid that may lead to inflammation or depression. Leg and hip fat may tend to be composed of omega three fatty acids which are healthier. For, e.g., middle-aged women, having a large WHR may be associated with a similar cardiovascular risk as that caused by smoking, low exercise levels, weight gain during adulthood, or higher caloric intake. A large waist may also be linked with anxiety and anger.

Central obesity for men may be defined as having a WHR greater than 1.0 for men and 0.92 for women. A pear-shaped body, which may be free of central obesity, may be defined as having a WHR of 0.89 for men and 0.80 for women. The waist circumference may be measured at the high point of the ileac crest and the hips circumference may be measured at the greatest circumference position. In general, the range of WHR may be described as follows:

| Waist Hip Ratio (WHR) Norms | | | | |
| --- | --- | --- | --- | --- |
| Gender | Excellent | Good | Average | At Risk |
| Male | <0.85 | 0.85-0.89 | 0.90-0.95 | >0.95 |
| Female | <0.75 | 0.75-0.79 | 0.80-0.86 | >0.86 |

Another important health indicator is the body mass index (BMI). Body mass index (BMI) and WHR are not necessarily related. FIGS. 5A-5B, although not drawn to scale, illustrate examples of BMI and WHR of different users. User 510 may have a BMI of 24 while user 520 may have a BMI of 35. User 510 may have a waist length of 80 cm and a hips length of 100 cm. User 520 may have a waist length of 100 cm and a hips length of 125 cm. Although users 510 and 520 may have different waist and hip sizes, they may have the same WHR of 0.80.

Abdominal fat may be used as a marker of visceral fat which is stored around important internal organs such as the liver, pancreas, or intestines. Abdominal fat may have greater blood flow and more receptors for cortisol than peripheral fat. In general, the greater the number of cortisol receptors, the more sensitive the visceral fat tissue may be to cortisol. Hence, people with higher abdominal fat (e.g., belly fat, waist fat) may have higher reactivity or sensitivity to stress. Likewise, people with higher reactivity or sensitivity to stress may have more abdominal fat (e.g., belly fat, waist fat). This heightened reactivity or sensitivity to cortisol may stimulate fat cells to further increase in size. Women who have a combination of normal BMI and high WHR may experience elevated cortisol reactivity to acute stressors and more failure to habituate to repeated stressors, comparing to women with normal WHR. This suggests that high WHR may also indicate Limbic-Hypothalamic-Pituitary-Adrenal axis (LHPA axis) dysregulation and over-exposure to cortisol.

Excessive central fat may be problematic for health. As explained above, excessive central fat may indicate greater visceral fat, which is morphologically different from peripheral fat. Visceral fat may have greater blood flow and up to four times more glucocorticoid receptors than peripheral fat. People having excessive central fat may be especially sensitive to the fat-accumulating effects of circulating cortisol and triglycerides. Visceral fat tissue may respond to circulating cortisol by further increasing the size of visceral fat tissue. Large central fat deposits may contribute to disease in part by releasing free fatty acids into the portal circulation, which can promote other risk factors, such as synthesis of cholesterol and insulin resistance. Central fat distribution may be related to adverse psychological states, such as depression and anxiety, and to social difficulties, such as unemployment and divorce. People having excessive central fat may have greater vulnerability to stress increases. A greater vulnerability to stress increase may increase exposure to stress-induced cortisol, which may in turn fuel central fat deposition.

WHR may be related to LHPA axis activation. The stress hormone cortisol, released after episodes of chronic stress, may be regulated by the LHPA axis. The stress hormone cortisol may be associated with higher levels of abdominal fat and higher WHR. The LHPA axis activation and corresponding SVB (sympathovagal balance) disturbance may be higher in people having higher cortisol levels.

WHR can be used for managing body shape. Decreasing stress or improving stress resilience may be a critical factor for one to lower their WHR, although decreasing stress or improving stress resilience need not directly lead to lower WHR. Improving stress resilience by breathing-based methods that require lower latency (faster reacting) SVB analysis may prevent a cortisol-based causality leading to an ever increasing WHR. The bidirectional relationship of increasing WHR being linked to reduced stress resilience and conversely improving stress resilience leading to a lower wait-to-hip ratio (WHR) can be used to manage body shape and other health conditions.

Monitoring WHR can be used as a guide for diet. Estrogen tends to store fat in hips, while cortisol tends to store fat in waist. If one has increased testosterone production or supplemented testosterone, which may reduce cortisol but increase estrogen due to aromatization, one may reduce fat storage in the waist and increase fat storage in the hips. Eating a higher proportion of fats and carbohydrates to protein may have a similar effect of increasing estrogen-cortisol ratio. Moreover, low-carb diets may increase stress and may make it harder to reduce WHR. Since both stress resilience and LHPA axis (Limbic-Hypothalamic-Pituitary-Adrenal axis) activation may be key markers of semi-autonomic control, monitoring them may provide feedback on an actionable aspect of WHR control.

Stress may be the body's reactions (e.g., biochemical reaction or physiological reaction) to an event that stimulates a physical, mental and/or emotional adjustment or response. Stress may be categorized into two different type: acute stress and chronic stress. Acute stress may result from specific events that may involve novelty, unpredictability, a threat to the ego, or a poor sense of control. As an example and not by way of limitation, acute stress can be associated with events like giving a speech in front of people or almost getting into an accident. Acute stress can be good because the stress hormones that released during an episode of acute stress may help one's mind and body to deal with the situation.

Chronic stress may result from repeated exposure to situations that lead to the release of stress hormones such as cortisol. Chronic stress can cause wear or tear on one's mind and body. Chronic stress may be linked to heart disease, high blood pressure, high cholesterol, type II diabetes, or depression. Stress resilience may be used to describe the acquired ability to meet life's challenges (e.g., stimulus that causes stress), to bounce back from challenging experiences, and to become more capable as a result. As described more fully below, stress resilience may be measured by how long it takes to recover from a stressed state to normal state. High stress resilience may be indicated by a shorter time to recover to normal state. Higher stress resilience may be associated with better health outcomes.

Chronic stress may trigger LHPA axis activation which may increase insulin levels and/or increase cortisol levels. Increased cortisol levels may have many consequences including, for example, but not limited to, increased weight gain, leading to obesity or excessive cortisol receptors in the belly fat. Cortisol release may increase appetite, anxiety, depression, apathy, activation of lipoprotein lipase, deposit of visceral fat, and may decrease the rate at which body fat breaks down.

In particular embodiments, a person's stress may be estimated or measured by monitoring that person's heart rate and activity level. In particular embodiments, heart rate may be measured by one or more heart rate sensors including, for example, but not limited to, an ECG (electrocardiography) sensor, a PPG (photoplethysmography) sensor, or other suitable heart rate sensors. In particular embodiments, a heart rate sensor may be disposed on or in one or more wearable devices or mobile devices, such as a smart watch or a similar wearable device. In particular embodiments, the activity level of a user may be monitored by an accelerometer or other sensors. In particular embodiments, the accelerometer or other sensors for monitoring a user's activity level may be disposed within one or more wearable devices or mobile devices, such as, a smart watch, a smartphone, or a tablet computer.

Figure 6:
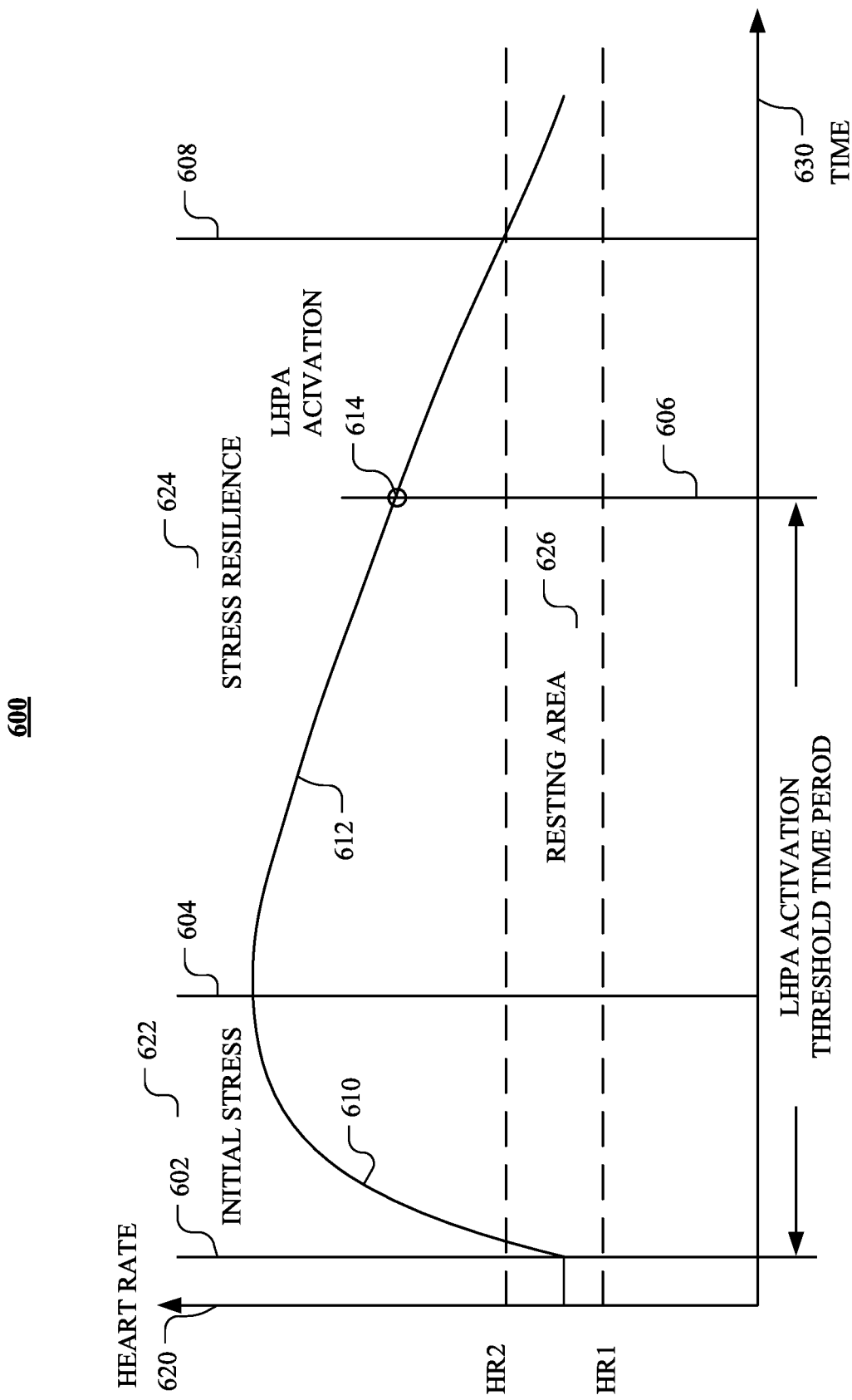
FIG. 6 illustrates an example graph of heart rate vs. time, and example stress-related portions of the graph.

FIG. 6 illustrates an example graph of heart rate vs. time, and example stress-related portions of the graph. In FIG. 6, axis 620 corresponds to heart rate and axis 630 corresponds to time. An episode of chronic stress may have multiple stages such as an initial stress stage 622 and a stress resilience stage 624. The initial stress stage 622 may have a start time 602 indicated by the heart rate starting to increase and may have an end time 604 indicated by the heart rate peaking, as illustrated by heart rate 610 during the initial stress stage 622. The initial stress stage 622 may have a heart rate increasing over time and exceeding the maximum resting heart rate HR2 of a user's resting heart-rate area 626. The resting area 626 may be defined by the maximum resting heart rate HR2 and the minimum resting heart rate HR1. Different individuals may have different values for the maximum resting heart rate HR2 and the minimum resting heart rate HR1. The stress resilience stage 624 may start from the end of the initial stress stage 622 and may end at the return time 608 of the user's heart rate to the resting area 626. In particular embodiments, stress resilience may be described by how long it takes for the user to recover to the resting area from a chronic stress. In general, a shorter recovery time from chronic stress may indicate a better stress resilience. In particular embodiment, stress resilience may be described by a speed in which a user recovers from chronic stress. The chronic stress episode and portions of the graph thereof illustrated in FIG. 6 are for example purpose only and are not intended to limit the systems and methods described herein.

Chronic stress may trigger LHPA axis activation, which leads to harmful cortisol release. The LHPA axis activation may start cortisol releasing after an LHPA axis activation threshold time period with respect to initial stress stage. In particular embodiments, the LHPA axis activation threshold time period may be defined as the time 602 from the start of the initial stress stage 622 to the time of the LHPA axis activation 614. The LHPA axis activation threshold time period may have a typical value of about 25 minutes. Different individuals may have different LHPA axis activation time period. In general, the LHPA axis activation threshold time period may be about 25±5 minutes. As an example and not by way of limitation, a first individual may have an LHPA axis activation threshold time period of 25 minutes. As an example and not by way of limitation, a second individual may have an LHPA axis activation threshold time period of 23 minutes. As an example and not by way of limitation, a third individual may have an LHPA axis activation threshold time period of 28 minutes. In particular embodiments, a health-monitoring system may detect an LHPA axis activation event based on the measured period of stress. In particular embodiments, the system may deduce the cortisol release time depending on the stress intensity and the period of the stress. In particular embodiments, the system may determine an LHPA axis activation event when the LHPA axis activation threshold time period has ended and the heart rate of the user is still higher than resting heart rate. As an example and not by way of limitation, a user may have an LHPA axis activation threshold hold time period of 25 minutes. The system may deduce an LHPA axis activation with cortisol release when the system detects that the heart rate of the user is higher than the maximum resting heart rate 25 minutes after a stress episode has begun.

Stress resilience may determine whether or not the LHPA axis activation will actually happen to a user experiencing an episode of chronic stress. If the user has a relative short stress resilience time period, the user's heart rate may enter the resting area within the LHPA axis activation threshold hold time period and LHPA axis activation may not happen. On the other hand, if the user has a relative long stress resilience time period, the user's heart rate may still be higher than the maximum resting heart rate when the LHPA axis activation time period ends, and thus LHPA axis activation may occur. In the example illustrated in FIG. 6, the heart rate is still higher than the maximum resting heart rate HR2 when the LHPA axis activation threshold time period ends and the LHPA axis activation 614 occurs at the end of the LHPA axis activation threshold time period 606. LHPA axis activation may be associated with cortisol release, which may increase waist fat formation. As described more fully herein, in particular embodiments the LHPA axis activation threshold time period may be measured for a user and feedback may be provided to that user before LHPA axis activation to prevent cortisol from releasing. The feedback may include early warning or stress management that can reduce or prevent potential cortisol release.

As described more fully herein, embodiments of present disclosure may determine an individual's LHPA axis activation threshold time period and use the determined time period to, for example, provide feedback to the individual before cortisol is released during an episode of stress. In other words, particular embodiments may use that individual's LHPA axis activation threshold time period to predict LHPA axis activation before activation has actually occurred during an episode of stress. In particular embodiment, an individual's determined LHPA axis activation threshold time period may be adjusted based on changes in the individual's waist-hip measurement (e.g., waist size, WHR) over a period of time. In particular embodiments, a user's determined LHPA axis activation threshold time period may be reduced when feedback to the user fails to prevent LHPA axis activation and cortisol release. In particular embodiments, a user's LHPA axis activation threshold time period may be adjusted by comparing the current LHPA axis activation threshold time period to one or more empirically measured stress resilience time periods based on the episodes or lack of episodes of the LHPA axis activation. As an example and not by way of limitation, if the system detects an increase WHR in response to stress, the current determined LHPA axis activation threshold time period for that user may be too long, i.e., the determined time period is longer than the user's actual time period. As an example and not by way of limitation, if the system detects the WHR having no increase in response to stress, the for that user may be too long, i.e., the determined time period is shorter than the user's actual time period. In particular embodiments, the system may determine an accurate LHPA axis activation threshold time period for the user based on the comparison of the current determined LHPA axis activation threshold time period with one or more empirically determined LPHA activation times periods and/or the stress resilience time periods.

Acute stress and chronic stress may be distinguished based on heart rate and activity measurement. As discussed above, the stress related parameters may be measured based on measurement of heart rate and/or activity of user. In particular embodiments, a user's heart rate may be measured by one or more heart rate sensors and the measurement data may be used to distinguish chronic stress from acute stress. In general, acute stress may be shorter in time than chronic stress. As an example and not by way of limitation, an episode of acute stress may have a typical lasting time of several seconds and may not last longer than 10 minutes. As an example and not by way of limitation, an episode of chronic stress may last much longer than acute stress, for example, from minutes to tens of minutes. Acute stress may also be more intense whereas chronic stress may have lower intensity. In other words, acute stress may be associated with higher heart rate levels than is chronic stress. In particular embodiments, acute stress and chronic stress may be distinguished based on data from heart rate measurements. In particular embodiments, acute stress and chronic stress may be distinguished based on data from activity measurement. In particular embodiments, acute stress and chronic stress may be distinguished based on data from both heart rate measurement and activity measurement. In particular embodiments, acute stress and chronic stress may be distinguished based on one or more measured stress parameters, one or more inferred parameters, a change over time of one or more parameters, or correlations between the parameters.

In particular embodiments, data from on one or more bio-sensors (e.g., ECG, PPG, accelerometer) may be monitored and collected from a user, e.g., to measure that user's heart rate, activity, or other related parameters. In particular embodiment, the sensing period (i.e., sampling period or measurement period) or frequency may be adaptive and adjusted based on a number of factors. In particular embodiments, the sensing period may be adjusted based on the user's heart rate, the data from accelerometer, or a combination of both. As an example and not by way of limitation, the sensing period may be adjusted to a shorter time period corresponding to a higher measurement frequency when a user's heart rate increases and/or the user's activity becomes more intense. As an example and not by way of limitation, the sensing period may be adjusted to a longer time period time corresponding to a lower measurement frequency when the user's has a relatively low heart rate (e.g., when the user's heart rate is within their resting area) or the user's activity is less intense. In particular embodiments, the sampling period may be adjusted based on stress type. As an example and not by way of limitation, the sampling period may be adjusted to a first time period for acute stress and may be adjusted to a second time period different from the first time period for chronic stress. In particular embodiments, the first time period for acute stress may be a shorter than the second time period for chronic stress.

In particular embodiments, stress detection may be based on one or more stress related parameters or a combination of multiple parameters. In particular embodiment, stress detection may be based on indirect parameters determined based on one or more measured parameters. In particular embodiments, the detection of stress may be based on a change over time for one or more parameters. In particular embodiments, the detection of stress may be based on correlations between one or more parameters. U.S. Patent Application Publication No. 2017/0071523, which is incorporated herein by reference, describes techniques for detecting and classifying stress.

Stress parameters (e.g., stress resilience) and WHR may have a bi-directional relationship and may influence each other in various ways. Conventionally, waist size may be manually measured using a tape. The tape-based measurement may have different disadvantages, such as lack of accuracy and lack of privacy, and is labor intensive. For tape-based measurement, the measurement accuracy is highly dependent on the location of the tape in the body and the tightness of placement, which are difficult to control consistently. The type of the tape may also affect the measurement results. The tape-based measurement may require another person to conduct the measurement and may need to remove clothes, which may lead to major privacy concerns for some people. The tape-based measurement may also be time consuming. In particular embodiments, waist and hips related parameters may be measured using one or more cameras associated with mobile device (e.g., smartphone camera) to determine waist circumference, waist length, hip circumference, hip length, and/or the WHR. In particular embodiments, the system may allow the user to enter measurements through user interfaces of the application. In particular embodiments, the system may determine the body shape of the user using contour detection and shape matching with different template body shapes. In particular embodiments, the body shape of the user may be used to improve the accuracy of waist-hip measurement, such as the WHR measurement.

In particular embodiments, in order to measure the waist by using a smartphone camera, the user may need to provide a comparative object. In particular embodiments, the comparative object may be a reference body part of the user, for example, a finger-span, a wrist, a hand, or other parts of body. In particular embodiments, the finger-span being used as baseline for measurement may be between the tips of the index finger and the thumb. In particular embodiments, the finger-span may be between any two fingers of the user hand. In particular embodiments, the dimension of the reference body part may be measured by comparing to a reference object with known dimension using an image of the reference body part and the reference object. In particular embodiments, the reference objects may be a ruler with dimensional markers.

Figure 7A:
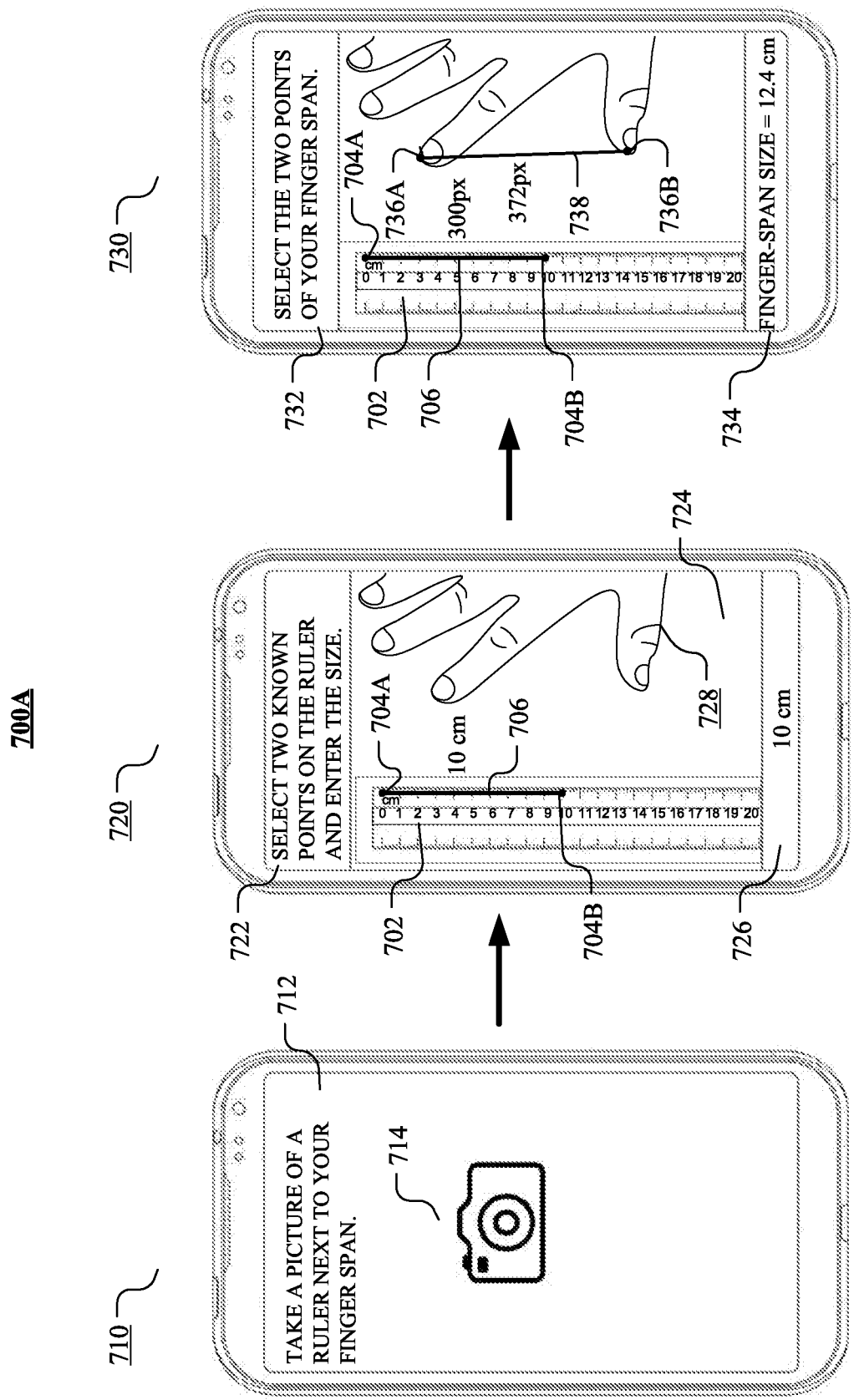
FIG. 7A illustrates example user interfaces for measuring a finger-span length based on image of the finger-span with a ruler as the reference object.

FIG. 7A illustrates example user interfaces for measuring a finger-span length based on image of the finger-span with a ruler as the reference object. In particular embodiments, the first step for measuring a finger-span length may be to initialize the system with an image of the finger-span (e.g., a hand in an L shape) and a reference object (e.g., a ruler) with known dimension within the same image. The user interface 710 illustrates a user interface having an instruction text box 712 and a camera icon 714 for the initialization step. The instruction text box 712 may include text describing actions that the user can take, for example, taking a picture of a ruler and a finger-span of the user. The camera icon 714 may be associated with the functionality of taking a picture with a camera (e.g., a rear camera, a front camera) of the device. As an example and not by way of limitation, the user may tap on the icon 714 to activate a camera mode for taking a picture. In particular embodiments, the camera may be a rear camera of the device. In particular embodiments, the camera may be a front camera of the device. In particular embodiments, the camera may be a separate camera connected to the device through a wired or wireless connection. In particular embodiments, the user may take a picture of the finger-span and the ruler using the camera of the device. In particular embodiment, the fingers of the user may be in the same planar plane (e.g., a desk surface) with the ruler when the picture is taken. In particular embodiments, the device may be positioned so that the camera has an image plane parallel to the planar plane (e.g., a desk surface) of the fingers and ruler. In particular embodiments, the user hand may be positioned in L shape next to the ruler on the planar plane. In particular embodiments, the system may take the picture and save the picture in a data store.

The user interface 720 illustrates a user interface for determining a dimension on the ruler 702 using the picture of the finger-span of a user hand 728 and the ruler 702. The user interface 720 may have an instruction text box 722, an image displaying area 724, and a text box 726. In particular embodiments, the instruction text box 722 may include text describing actions that the user can take in this step, for example, selecting two known points (e.g., 704A, 704B) on the ruler and entering the size (i.e., length) between the two points (e.g., 10 cm). In particular embodiments, the user may determine the length between the two points of the ruler by directly reading the dimension of the ruler. The image displaying area 724 may display the image of the finger-span and ruler. The length between the two points (704A, 704B) may be entered in the text box 726 and may be displayed both in the text box 726 and near the line 706 between the two points (704A, 704B). In particular embodiments, the length of the line 706 between the two points (704A, 704B) can be determined automatically using image processing algorithms with no need for the user to enter the length. In particular embodiments, the dimension of the ruler or other reference object may be determined automatically using image processing algorithms with no need for the user to select the two points.

The user interface 730 illustrates a user interface for determining the finger-span length using the picture of the finger-span and the ruler. The user interface 730 may have an instruction text box 732, an image displaying area 724, and a displaying text box 734. The instruction text box 732 may include text describing actions that the user can take in this step, for example, selecting two points of the finger-span. The image displaying area 724 may display the image of the finger-span and ruler. The displaying text box 734 may display the finger-span size in text and numbers. In particular embodiments, the system may allow the user to select two points (736A, 736B) in the picture corresponding to the length of the finger-span. In particular embodiments, the two points corresponding to the length of the finger-span may include a first point at the end of index finger and a second point at the end of thumb. In particular embodiments, the two points may include other points corresponding to the dimension of the reference body part, for example, wrist length. The distance between the two points (736A, 736B) may indicate the length of the finger-span 738. In particular embodiments, the system may determine the number of pixels between the two points of the ruler (704A, 704B) and the number of the pixels between the two points of the finger-span (736A, 736B). In particular embodiments, the system may determine the length of the finger-span based on the length of the line 706 between the two points of the ruler (704A, 704B), the number of pixels between the two points of the ruler (704A, 704B), and the number of the pixels between the two points of the finger-span (736A, 736B). As an example and not by way of limitation, the 10 cm length in the picture may be corresponding to 300 pixels and the finger-span length may be corresponding to 372 pixels, then the finger-span length may be 12.4 cm. In particular embodiments, the dimensions of the hand including the finger-span length, may be determined using cross product calculation. In particular embodiments, the dimensions of the hand may be determined automatically by using image processing algorithms such as a contour detecting algorithm. In particular embodiments, the system may receive the pre-measured length of the finger-span from the user. The pre-measured length of the finger-span may be manually measured by the user using a ruler. In particular embodiments, the system may store the length of the finger-span in a data store of the system and the stored length of the finger-span may be retrieved later by the system. In particular embodiments, the system may store the image taken in the initialization of the system for determining the finger-span length in a data store and the stored image may be retrieved by the system for re-calibrating the system.

Figure 7B:
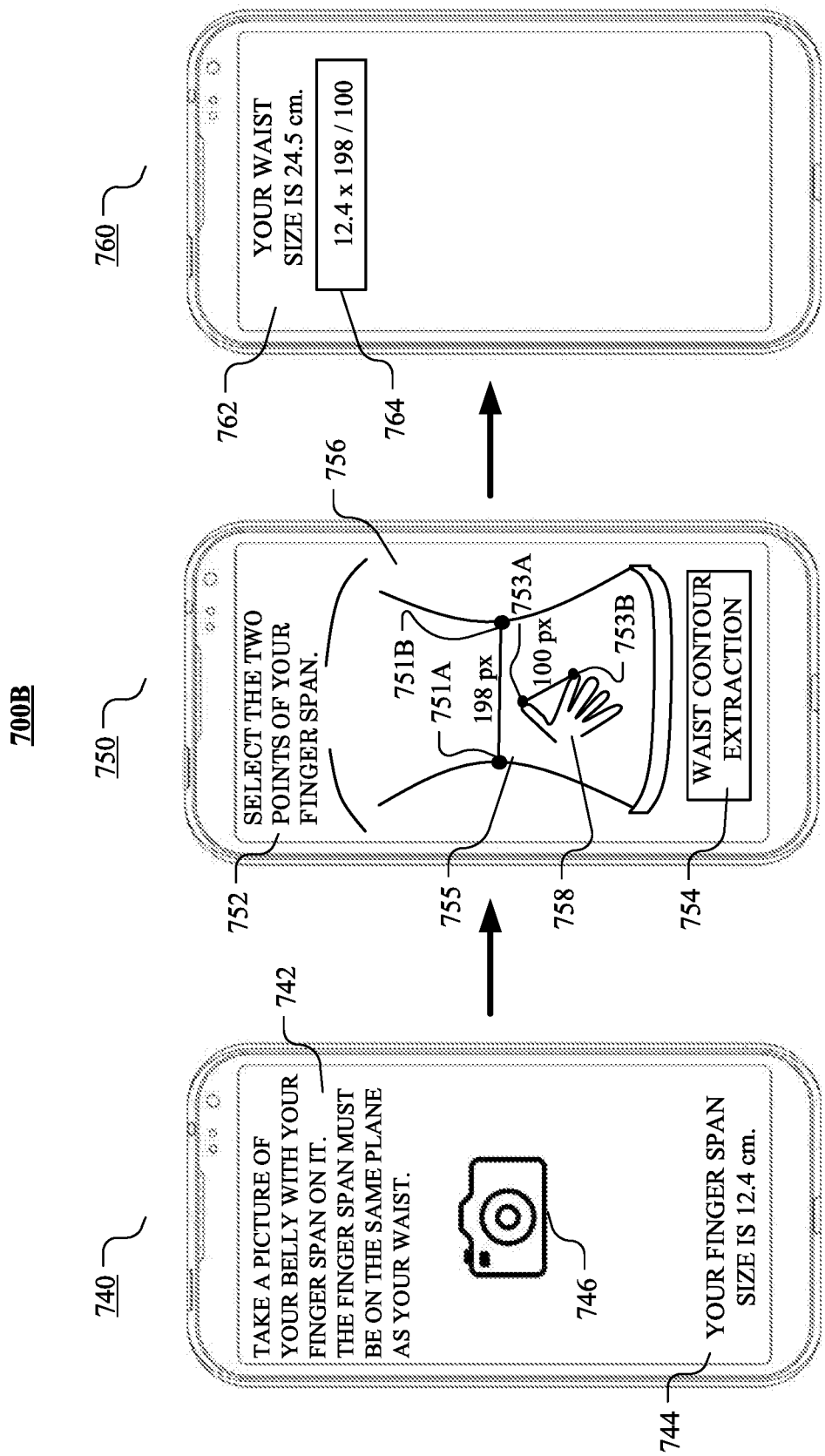
FIG. 7B illustrates example user interfaces for measuring the waist size based on images of the waist and the finger-span.

FIG. 7B illustrates example user interfaces for measuring waist size based on image of the waist and the finger-span of the user. In particular embodiments, when the user wants to measure their waist size, the user may take a picture that includes their hand next to their waist. In particular embodiments, the system may allow the user to select two points in the picture for the waist and two point for the finger span, respectively. The two points for the waist may be corresponding to the waist size in the picture and the two points for the finger-span may correspond to the length of the finger-span. In particular embodiments, the system may determine the waist size based at least in part on the positions of the user-selected points. In particular embodiments, the system may automatically calculate the waist size based on the picture of the waist and the hand using image processing algorithms. While FIGS. 7A-7B illustrated example interfaces, this disclosure contemplates any suitable interfaces for determining a user's finger span, waist size, or both.

The user interface 740 illustrates a user interface for taking picture for the waist of the user. The user interface 740 may have an instruction text box 742, a camera icon 746, and a display text box 744. The instruction text box 742 may include text describing actions that the user can take. The display text box 744 may display the finger-span size as determined or received from former steps. The camera icon 746 may be associated with picture-taking functionality of the device. For example, the user may tap on the camera icon 746 to activate the picture taking mode for the camera of the device. In particular embodiments, the user may take one or more pictures of the waist and the finger-span of the user using the user interface 740 and the system may save the one or more pictures in a data store for later usage.

The user interface 750 illustrates a user interface for determining the waist size using the picture including the waist and finger-span of the user. The user interface 750 may have an instruction text box 752, an image display area 756, and a text box button 754. The instruction text box 752 may include text describing actions that the user can take in this step. The image display area 756 may display the image of the waist 755 and the finger-span 758 of the user. The text box button 754 may display text (e.g., waist contour extraction) describing a functionality of the system, for example, determining the waist size using contour extraction. The user may tap on the text box button 754 to trigger the system to determine the waist size automatically using image processing algorithms such as contour extraction.

In particular embodiments, the system may determine the waist size using a similar process as in determining the finger-span length. In particular embodiments, the system may allow the user to select two points (e.g., 753A, 753B) in the image corresponding to the finger-span length and may determine the number of pixels (e.g., 100 pixels) between the two points. In particular embodiments, the system may allow the user to select two points (e.g., 751A, 751B) in the image corresponding to the waist length and the system may determine the number of pixels (e.g., 198 pixels) between the points. In particular embodiments, the system may determine the waist length based on the number of pixels between the two points corresponding to the waist size, the number of the pixels between the two points corresponding to the finger-span length, and the finger-span length determined or received in former steps. As an example and not by way of limitation, the finger-span may correspond to 100 pixels in the picture and the waist length may correspond to 198 pixels, then the waist length may be determined as 24.5 cm given a finger-span length of 12.4 cm determined in former steps. In particular embodiments, the system may determine the waist circumference using a similar process as the waist length. In particular embodiments, the system may determine the waist circumference based at least in part on the determined waist length.

In particular embodiments, when the text box button 754 is tapped, the system may start an automatic process of waist and finger contour extraction using image processing algorithms and may determine the waist size and finger-span length with no need for the user to select the corresponding points in the picture. In particular embodiments, the system may automatically start the process of waist and finger contour extraction using image processing algorithms and may have no need for the user to tap on the text box button 754 or take any other action to trigger the process. In particular embodiments, the finger border and waist border may be automatically extracted by the system using a contour detection algorithm. In particular embodiments, the system may automatically determine the number of pixels corresponding to the waist size and the number of pixels corresponding to the finger-span length based on the image of the waist and finger-span using one or more image processing algorithms. In particular embodiments, the system may automatically determine the waist size based on the image of the waist and finger span using one or more image processing algorithms. As an example and not by way of limitation, the system may process the image using contour extraction to determine that the finger-span length corresponds to 100 pixels in the image and the waist length corresponds to 198 pixels in the image, then the system may determine that the waist length is 24.5 cm if the finger-span length is 12.4 cm.

In particular embodiments, the system may determine the body shape of the user using the contour detection and shape matching algorithms. In particular embodiments, the system may determine the body shape profile of the user based on the user's body shape. The body shape profile may be associated with a risk profile of the user. In particular embodiments, the system may determine the risk profile of the user based on the body shape profile of the user. In particular embodiments, the system may evaluate the risk of health problems based on WHR norms, which may be different for males and females, for example as follows:

| Waist Hip Ratio (WHR) Norms for Risk Evaluation | | | | | |
|---|---|---|---|---|---|
| Gender | Age | Low | Moderate | High | Very High |
| Female | 20-29 | <0.71 | 0.71-0.77 | 0.78-0.82 | >0.82 |
|  | 30-39 | <0.72 | 0.72-0.78 | 0.79-0.84 | >0.84 |
|  | 40-49 | <0.73 | 0.73-0.79 | 0.80-0.87 | >0.87 |
|  | 50-59 | <0.74 | 0.74-0.81 | 0.82-0.88 | >0.88 |
|  | 60-69 | <0.75 | 0.76-0.83 | 0.84-0.90 | >0.99 |
| Male | 20-29 | <0.83 | 0.83-0.88 | 0.89-0.94 | >0.94 |
|  | 30-39 | <0.84 | 0.84-0.91 | 0.92-0.96 | >0.96 |
|  | 40-49 | <0.88 | 0.88-0.95 | 0.96-1.00 | >1.00 |
|  | 50-59 | <0.90 | 0.90-0.96 | 0.97-1.02 | >1.02 |
|  | 60-69 | <0.91 | 0.91-0.98 | 0.99-1.03 | >1.03 |

In particular embodiments, the system may determine that a user has a convex waist shape using contour detection. In particular embodiments, the system may determine the waist size (e.g., waist length or waist circumference) based on a maximum waist size for the user having a convex waist shape. In particular embodiments, the system may search for the maximum size along the waist contour of the convex waist shape. In particular embodiments, the system may determine the user has a concave waist shape using contour detection. In particular embodiments, the system may determine the waist size based on a minimum waist size for a user having the concave waist shape. In particular embodiments, the system may search for the minimum size along the waist contour of the concave waist shape using algorithms. As an example and not by way of limitation, the user waist illustrated in the user interface 750 in FIG. 7B has a concave waist shape. The system may search for the minimum waist size along the waist contour using algorithms and may use the minimum waist size as the determined waist size of the user.

In particular embodiments, a combination of the automatic method (e.g., contour detection algorithm) and the manual method (e.g., allowing a user to select two points corresponding to finger-span and waist size, respectively) may be used in determining a user's waist size. As an example and not by way of limitation, the system may first try to determine the waist size and finger-span length using contour detection and may allow the user select the corresponding points in the image to improve precision. In particular embodiments, when the finger-span contours are difficult to find using computer vision and image processing algorithms, the system may allow the user to manually select the two points in the image corresponding to the finger-span length to have a better precision. In particular embodiments, when the waist shape contours are difficult to find using computer vision and image processing algorithm, the system may allow the user to manually select the two points in the image corresponding to the waist length to have a better precision. In particular embodiments, the system may allow the user to select some of the points in the image corresponding to the waist size and finger-span length and may use a contour detection algorithm for the remaining steps to determine the waist size.

The user interface 760 in FIG. 7B may display the result of the waist size measurement. The user interface 760 may have a display text box 762 including text describing the waist size, for example, a waist length of 24.5 cm. The user interface 760 may have another display text box 764 including text, numbers, or equations used for determining the waist size. While FIGS. 7A-7B illustrated example interfaces, this disclosure contemplates any suitable interfaces for determining and displaying a user's finger span, waist size, or both.

Figure 8:
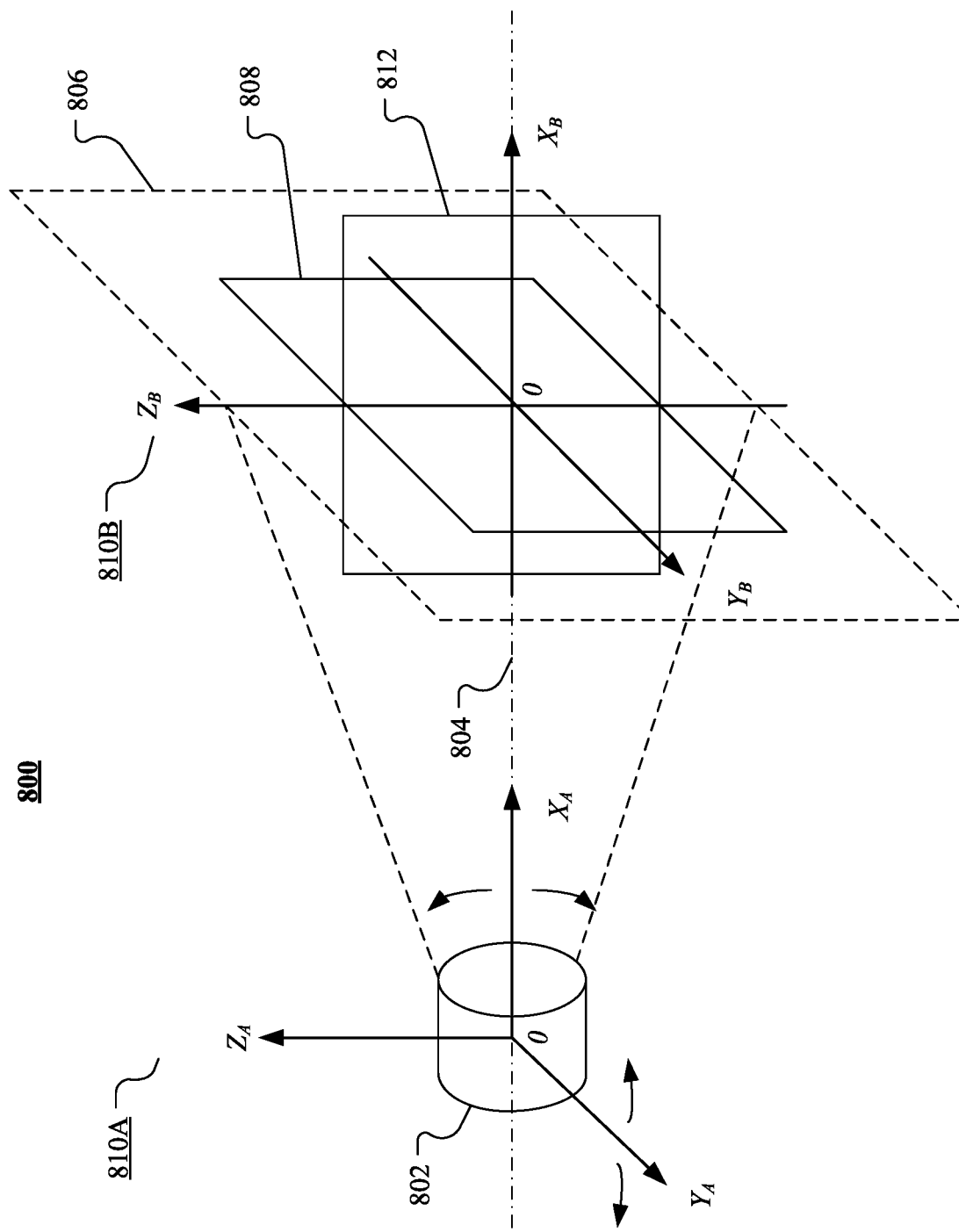
FIG. 8 illustrates an example configuration which has the camera image plane positioned with respect to the waist plane of user.

In particular embodiments, the camera, the finger-span, and the waist of the user may be positioned in specified manner for taking picture. FIG. 8 illustrates an example configuration which has the camera image plane positioned with respect to the waist plane of user. The camera 802 may have an optical axis 804 and may be positioned in a first Cartesian coordinate system 810A. The user waist and finger-span may be positioned in a second Cartesian coordinate system 810B. The first Cartesian coordinate system 810A may have the coordinate axis $X_A$, $Y_A$, $Z_A$ parallel to a corresponding coordinate axis $X_B$, $Y_B$, $Z_B$ of the second coordinate system 810B, respectively. The camera 802 may have an image plane 806 that is aligned with a plane 808 in the $Y_B$-$Z_B$ plane of the second coordinate system 810B. The optical axis 804 of the camera 802 may be perpendicular to the image plane 806.

In particular embodiments, the direction of the camera 802 may be adjusted in the three dimensions $X_A$, $Y_A$, $Z_A$ of the coordinate system 810A, for example, in the $X_A$-$Z_A$ plane or $X_A$-$Y_A$ plane of the coordinate system 810A. In particular embodiments, the system may receive feedback from an IMU (Inertial Measurement Unit) indicating the camera position (e.g., a distance to the user, angles in the three-dimensional space, etc.) with respect to the user's body. In particular embodiments, the IMU may be within the client device having the camera. In particular embodiments, the IMU may include a number of sensors including, for example, but not limited to, a three-axis accelerometer and a gyroscope. In particular embodiments, the device (e.g., a smartphone) having the camera 802 may be parallel to the finger-span plane in order to minimize image distortion. In particular embodiments, the position information of the device (e.g. height from ground, angles in the three-dimensional space, optical axis alignment) may be displayed or illustrated on the device screen in real time to allow the user to read the position information and adjust the device position accordingly.

In particular embodiments, the waist plane may be defined by a virtual cross section plane of the user waist. In particular embodiments, the user may stand straight up while taking the picture so that the user's body is aligned with the axis $Z_B$ of the coordinate system 810B. When the user stands straight along the axis $Z_B$ in the coordinate system 810B, the waist plane may be parallel to the $X_B$-$Y_B$ plane of the coordinate system 810B. In particular embodiments, the image plane 806 of the camera 802 may be perpendicular to the waist plane of the user when taking the picture. In particular embodiments, feedback from the IMU (Inertial Measurement Unit) may include an identification of the image plane perpendicular to the waist plane of the user. In particular embodiments, for taking the picture, the user may have the finger-span and the belly in the same planar surface 808 and the camera 802 may face the user's belly from the front of the user. The picture taken in this manner may be a font picture of the waist with the finer-span. In particular embodiments, the user may have the finger-span and the belly in the same planar surface 812 and the camera 802 may face the user's belly from the side of the user. The picture taken in this manner may be a side picture of the waist with the finger-span. In particular embodiments, the hand may be used as the reference body part and may be positioned in the same planar surface as the belly for a better precision. In particular embodiments, the wrist may be used as the reference body part and may be positioned in the same planar surface as the belly for a better precision.

In particular embodiments, the system may take picture from the front (e.g., with the camera facing the user's belly from front) of the user and determine the waist measurement based on the front image. In particular embodiments, the system may take picture from the side of the user (e.g., camera facing the user belly from side) and determine the waist measurement based on the side image. In particular embodiments, the system may take pictures both from the front side of the user and the side of the user and determine the waist measurement based on both of the font image and side image. In particular embodiments, when the user has large belly, the system may take a front picture of the belly and a side picture of the belly and determine the waist size based on both pictures to maximize the accuracy. In particular embodiments, the system may use the larger waist size determined from a front image and a side image as the determined waist size of the user.

In particular embodiments, the waist size measurement may be the waist length measurement using the process a discussed above. In particular embodiments, the waist size measurement may be the waist circumference measurement using a similar approach. In particular embodiments, the system may measure any related parameters based on the same or similar approach. In the particular embodiments the parameters measured by the system may be dimensional with unit, for example, but not limited to, a length, a height, a width, a distance, or a circumference. In particular embodiments, the parameters measured by the system may be dimensionless, for example, but not limited to, a ratio.

Figure 9A:
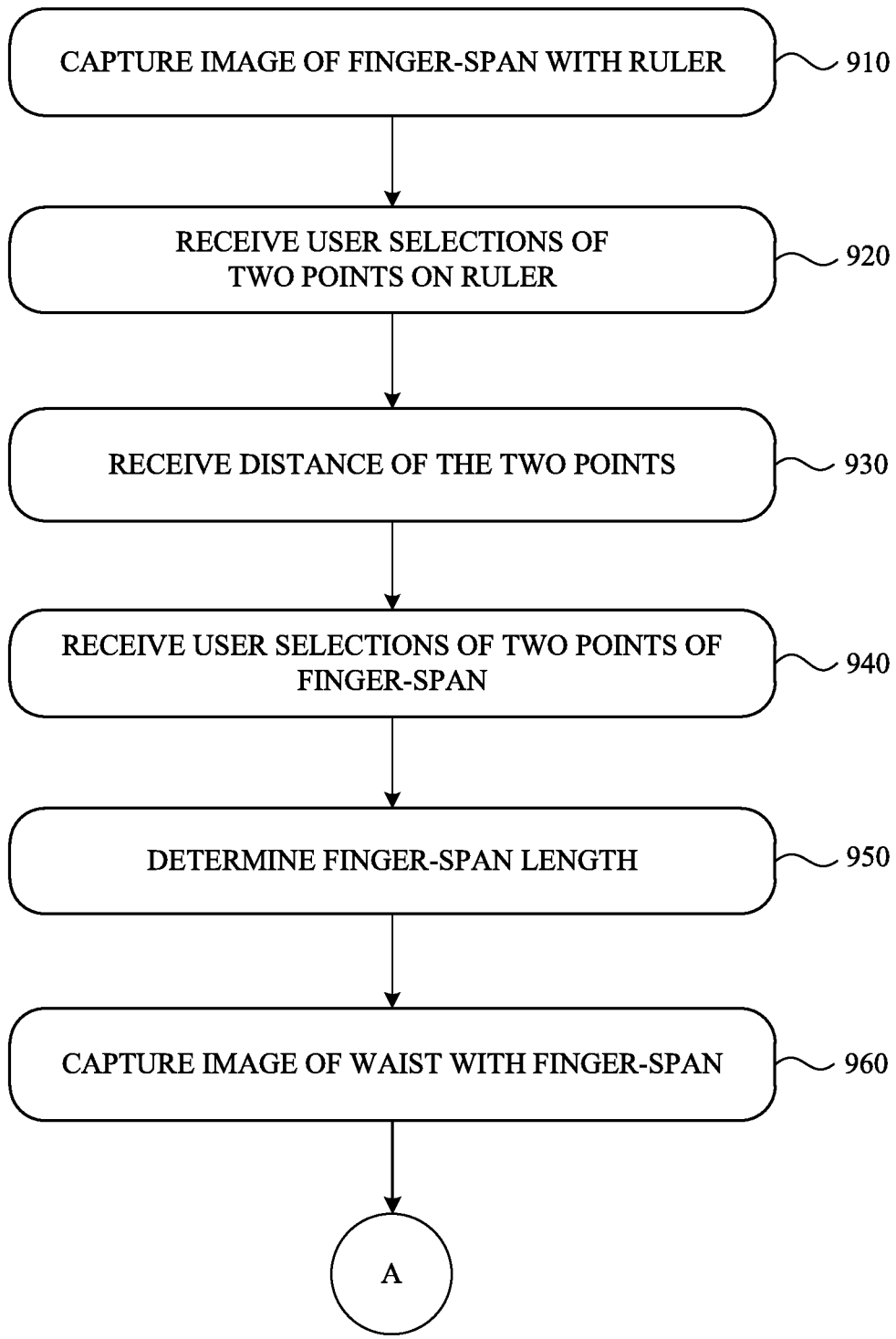
FIGS. 9A-9B illustrate an example method for determining a finger-span length and waist size of a user based on images of the finger-span and waist.
Figure 9B:
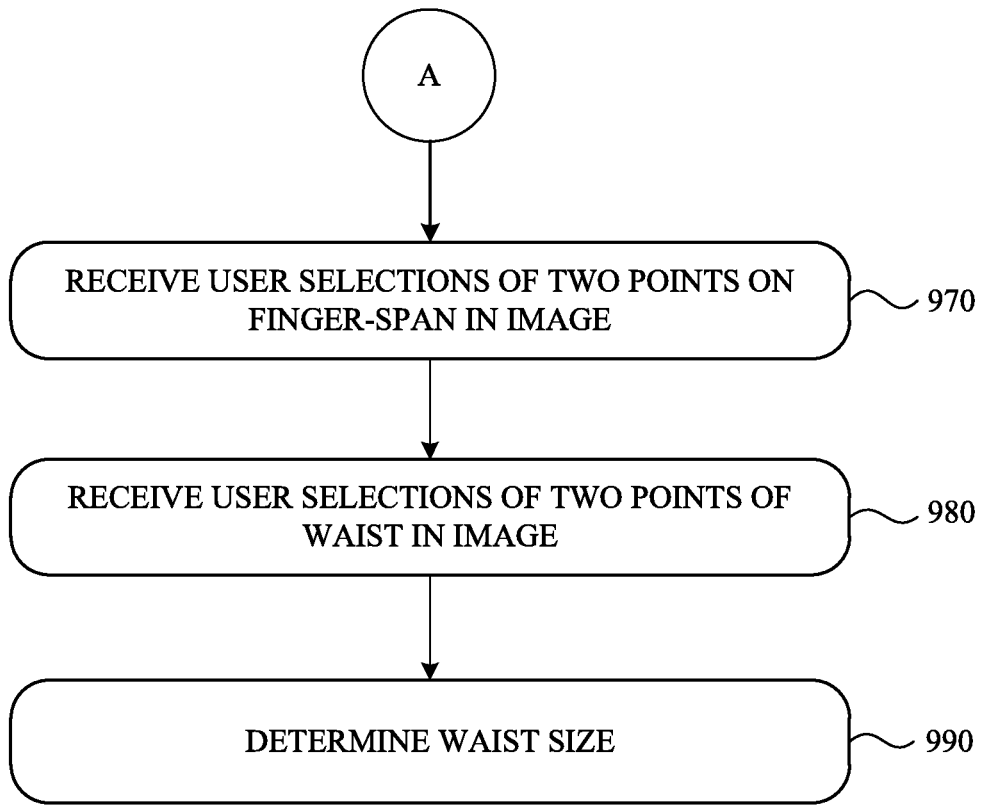

FIGS. 9A-9B illustrate an example method for determining a finger-span length and waist size of a user based on images of the finger-span and waist. The method may use the same or similar user interfaces illustrated in FIGS. 7A-7B. In step 910, the system may capture an image of the user's finger span and a ruler next to the finger span. The ruler and the finger span of the user may be on the same planar surface, for example, a desk surface. In step 920, the system may receive user selections of two points in the image on the ruler. The system may determine the number of the pixels of the image corresponding to the length of the line connecting the two points on the ruler. In step 930, the system may receive the distance (e.g., 10 cm) between the two selected points on the ruler (i.e., the length of the line connecting the two points). In step 940, the system may receive user selections of two points in the image corresponding to the length of the finger span. The system may determine the number of pixels between the two points corresponding to the length of the finger span. In particular embodiments, the two points corresponding to the length of the finger span may include a first point at the end of the index finger and a second point at the end of the thumb. In particular embodiments, the two points may include other points corresponding to the dimension of the reference body part, for example, wrist length. In step 950, the system may determine the finger-span length based on the number of pixels corresponding to the length of the finger span, the number of pixels between the user-selected two points on the ruler, and the distance between the user-selected two points on the ruler. In step 960, the system may capture an image of the waist with the finger span within the same image. The finger span may be positioned in the same planar surface as the user's belly when taking the picture. In step 970, the system may receive user selections of two points in the image of the waist and finger span. The two points may correspond to the length of the finger span in the image. In step 980, the system may receive user selections of the two points in the image corresponding to the waist size. The system may determine the number of pixels in the image corresponding to the length of the finger span and the number of pixels in the image corresponding to the waist size. In step 990, the system may determine the waist size based at least in part on the number of pixels corresponding to the length of the finger span, the number of pixels corresponding to the waist size, and the length of the finger span as determined in former steps. Although this disclosure describes and illustrates particular steps of the method of FIGS. 9A-9B as occurring in a particular order, this disclosure contemplates any suitable steps of the method of FIGS. 9A-9B occurring in any suitable order. Moreover, although this disclosure describes and illustrates an example method for determining a user's finger-span length and waist size based on images of the user's finger-span and waist including the particular steps of the method of FIGS. 9A-9B, this disclosure contemplates any suitable method for determining a user's finger-span length and waist size including any suitable steps, which may include all, some, or none of the steps of the method of FIGS. 9A-9B, where appropriate. Furthermore, although this disclosure describes and illustrates particular components, devices, or systems carrying out particular steps of the method of FIGS. 9A-9B, this disclosure contemplates any suitable combination of any suitable components, devices, or systems carrying out any suitable steps of the method of FIGS. 9A-9B.

Figure 10:
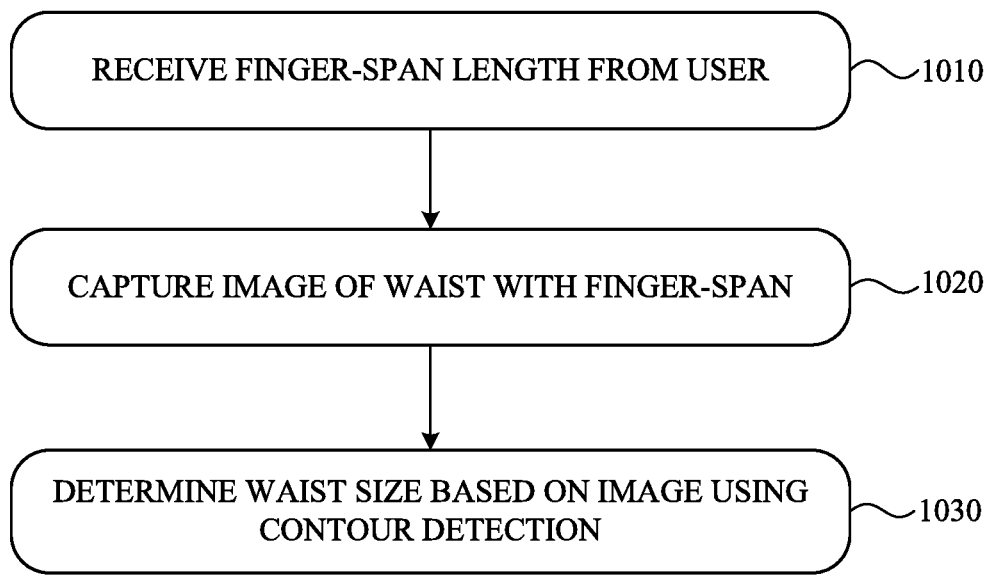
FIG. 10 illustrates an example method for receiving finger-span length from a user and determining the waist size of the user based on a waist image.

FIG. 10 illustrates an example method for receiving finger-span length from a user and determining the waist size of the user based on a waist image. In particular embodiments, the system may receive the length of the finger-span from the user and the system may not need to measure the length of the finger span. In step 1010, the system may receive the length of the finger span from the user. For example, the system may allow the user to type in the finger-span length through a user interface. In step 1020, the system may capture an image of the waist with the finger-span included in the image. The finger-span may be in the same planar surface as the belly of the user. In step 1030, the system may determine the waist size based on the image of the waist and finger span using a contour detection algorithm or other image processing algorithms. The waist size may be determined by comparing the waist size to the finger span in the image and may be calculated based on the pixel number corresponding to the waist size, the pixel number corresponding to the finger span, and the length of the finger span received in step 1010. Although this disclosure describes and illustrates particular steps of the method of FIG. 10 as occurring in a particular order, this disclosure contemplates any suitable steps of the method of FIG. 10 occurring in any suitable order. Moreover, although this disclosure describes and illustrates an example method for receiving finger-span length from a user and determining the user's waist size based on an image including the particular steps of the method of FIG. 10, this disclosure contemplates any suitable method for receiving finger-span length from a user and determining the user's waist size including any suitable steps, which may include all, some, or none of the steps of the method of FIG. 10, where appropriate. Furthermore, although this disclosure describes and illustrates particular components, devices, or systems carrying out particular steps of the method of FIG. 10, this disclosure contemplates any suitable combination of any suitable components, devices, or systems carrying out any suitable steps of the method of FIG. 10.

Figure 11:
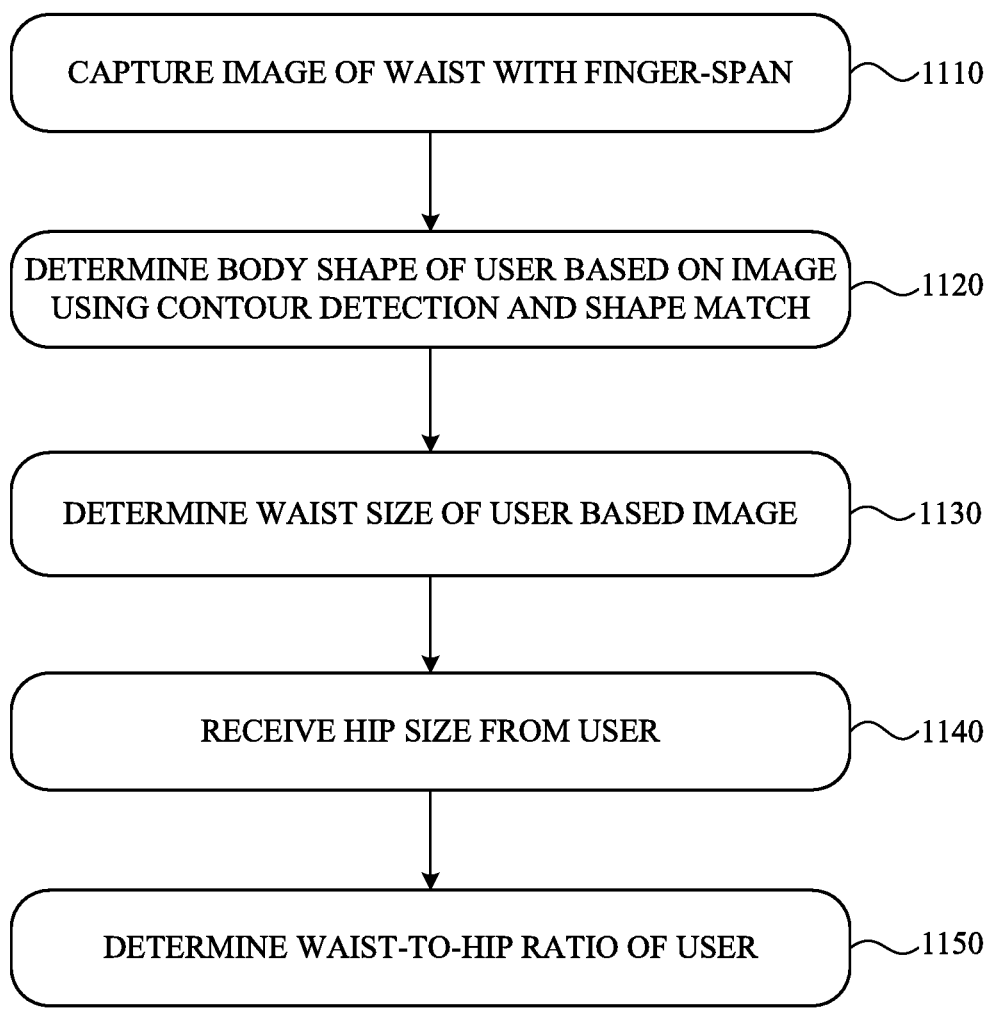
FIG. 11 illustrates an example method for receiving hip size from a user and determining the WHR of the user based on a waist image.

FIG. 11 illustrates an example method for receiving hip size from a user and determining the WHR of the user based on a waist image. In particular embodiments, the system may receive the hip size from the user and determine the WHR based on the received hip size. In step 1110, the system may capture an image of the waist with the finger span included in the same image. The finger span may be positioned in same planar surface with the belly of the user. In step 1120, the system may determine the body shape of the user based on the waist image. The body shape of the user may be determined using, e.g., a contour detection algorithm. In step 1130, the system may determine the waist size by comparing the waist size to the finger-span length based on the image of the waist and the finger span. The finger-span length may be determined or received during the initialization of the system. The finger-span length may be stored in a data store of the system after the initialization of the system. The finger-span length may be retrieved from a data store of the system. In step 1140, the system may receive the hip size from the user. In step 1150, the system may determine the WHR of the user based on the determined waist size and the hip size received in former steps. Although this disclosure describes and illustrates particular steps of the method of FIG. 11 as occurring in a particular order, this disclosure contemplates any suitable steps of the method of FIG. 11 occurring in any suitable order. Moreover, although this disclosure describes and illustrates an example method for receiving hip size from a user and determining the user's WHR including the particular steps of the method of FIG. 11, this disclosure contemplates any suitable method for receiving hip size from a user and determining the user's WHR based on an image including any suitable steps, which may include all, some, or none of the steps of the method of FIG. 11, where appropriate. Furthermore, although this disclosure describes and illustrates particular components, devices, or systems carrying out particular steps of the method of FIG. 11, this disclosure contemplates any suitable combination of any suitable components, devices, or systems carrying out any suitable steps of the method of FIG. 11.

Figure 12:
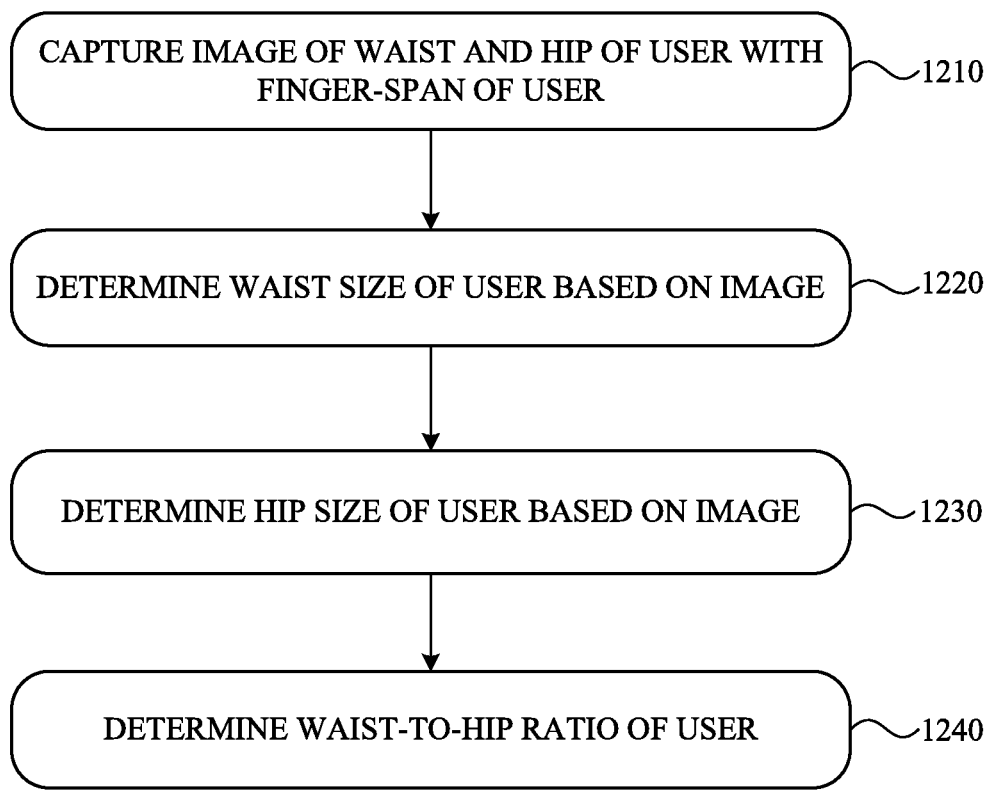
FIG. 12 illustrates an example method for determining a hip size and WHR of a user based on an image of the waist and hips of the user.

FIG. 12 illustrates an example method for determining a hip size and WHR of a user based on an image of the waist and hips of the user. In particular embodiments, the system may determine the waist size and the hip size of the user using the image including the waist, hip, and finger span. In step 1210, the system may capture an image of the waist with the hip and the finger span included in the same image. In particular embodiments, the camera may face toward the front of the user. The finger span may be positioned to be parallel to the image plane of the camera. In step 1220, the system may determine the waist size of the user based on image by comparing the waist size to the finger span length. The system may retrieve the stored finger span length from a data store of the system. In step 1230, the system may determine the hip size of the user based on the same image by comparing the hip size to the finger-span length. The hip size and the waist size may be determined using image processing algorithms such as a contour detection algorithm. In step 1240, the system may determine the WHR of the user based on the waist size and the hip size determined in the former steps. In particular embodiments, the system may store the determined waist size, hip size, and the WHR in a data store of the system. Although this disclosure describes and illustrates particular steps of the method of FIG. 12 as occurring in a particular order, this disclosure contemplates any suitable steps of the method of FIG. 12 occurring in any suitable order. Moreover, although this disclosure describes and illustrates an example method for determining a user's hip size and WHR including the particular steps of the method of FIG. 12, this disclosure contemplates any suitable method for determining a user's hip size and WHR based on an image including any suitable steps, which may include all, some, or none of the steps of the method of FIG. 12, where appropriate. Furthermore, although this disclosure describes and illustrates particular components, devices, or systems carrying out particular steps of the method of FIG. 12, this disclosure contemplates any suitable combination of any suitable components, devices, or systems carrying out any suitable steps of the method of FIG. 12.

Chronic stress, WHR, and other health outcomes may have a bi-directional influence and certain correlations, as explained below. In particular embodiments, the system may provide feedback through a client system to the user for recommending stress management techniques or other health management recommendations. In particular embodiments, the system may access the waist-hip measurement of the user. In particular embodiments, the waist-hip measurement may include measurement of a waist size (e.g., a waist length, a waist circumference), a hip size (e.g., a hip length, a hip circumference), and/or a WHR. In particular embodiments, the waist size and the hip size may be measured by the system based on the image of waist and hip. In particular embodiments, the hip size may be input into the system by the user.

In particular embodiments, the system may measure a number of stress-related parameters. The stress-related parameters may include, for example, but are not limited to, an acute stress, one or more acute stress episodes, a chronic stress, a period of chronic stress, a stress resilience, a period of stress resilience, an LHPA axis activation, and/or an LHPA axis activation threshold time period. Another stress-related parameter may be a user's heart rate during a time period including at least the time period of chronic stress and the period of stress resilience. The user's stress level and/or activity level may also be measured during that time period. Another stress-related parameter may be a user's heart rate during a time period of multiple days. The user's stress level and/or activity level may also be measured during that time period.

In particular embodiments, the system may determine one or more correlations between one or more waist-hip measurement and one or more stress-related parameters. In particular embodiments, the system may provide feedback to the user based on the stress-related parameters. In particular embodiments, the system may provide feedback to the user based on the correlations between the stress-related parameters and the waist-hip measurement. In particular embodiments, the system may provide feedback to the user if the high stress, the stress resilience, or the WHR have mutually destructive relationships. In particular embodiments, feedback may be provided to the user within the user's LHPA axis activation threshold time period (i.e., before an LHPA activation event) when the user is undergoing a period of stress. With the feedback, the user may be notified to immediately manage stress (or, at least, manage stress before expiration of the user's LHPA axis activation threshold time period) in order to reduce the user's heart rate to the resting area, thus preventing a potential cortisol release. In particular embodiment, the system may provide feedback to the user at the start of the LHPA axis activation to reduce the cortisol release or prevent a cortisol release from peaking. In particular embodiments, the system may deduce an LHPA axis activation and cortisol release event by monitoring the heart rate and determining that the heart rate is still higher than the user's resting heart rate at the end of the LHPA axis activation threshold time period. In particular embodiments, the system may determine the body shape of the user using contour detection and shape matching with different template body shapes. In particular embodiments, the system may determine the metabolic risk profile based on the body shape of the user and may further improve the analysis by the system using such risk profile information. In particular embodiments, the system may provide to the user the feedback including a risk profile associated with the body shape of the user.

Figure 13:
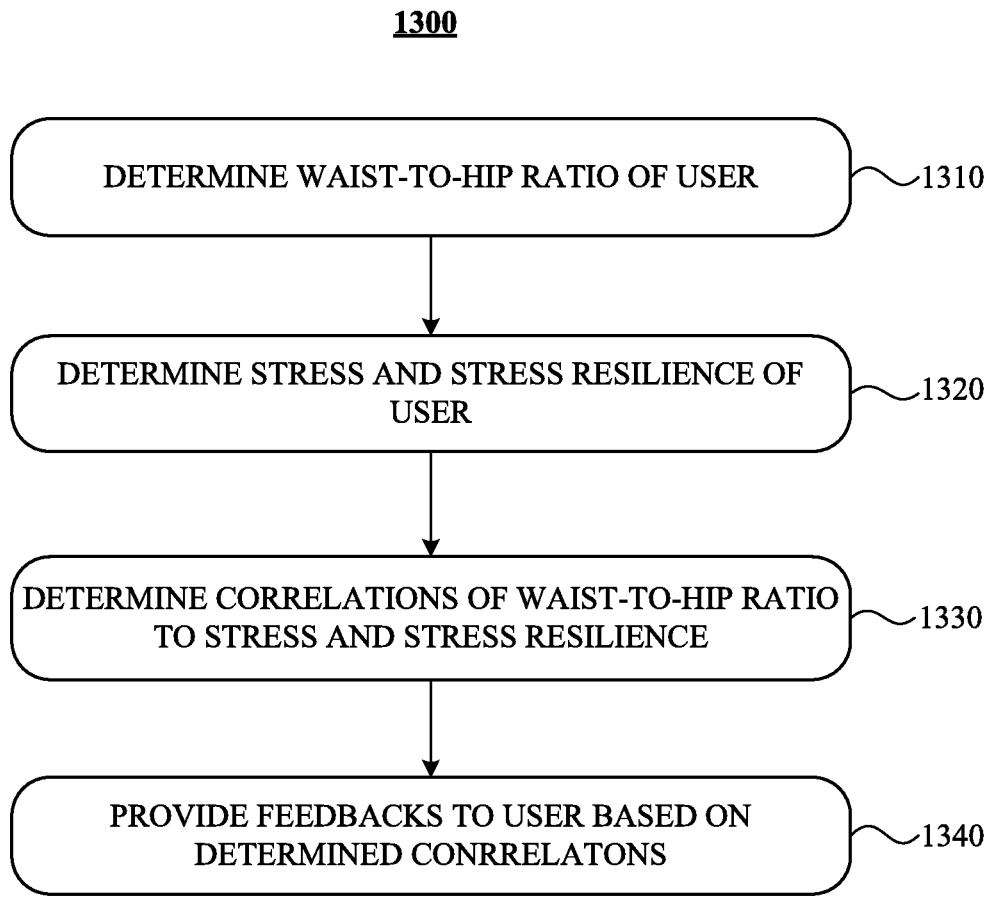
FIG. 13 illustrates an example method for determining correlations between the WHR, the stress, and the stress resilience of a user and providing feedback to the user based on the correlations.

FIG. 13 illustrates an example method for determining correlations between the waist-hip-ratio (WHR), stress (as determined by one or more stress-related parameters), and the stress resilience of a user and providing feedback to the user based on the correlations. In step 1310, the system may determine the WHR of the user. In particular embodiments, the system may record the determined WHR in a data store of the system or may determine the WHR by accessing it from a data store of the system. In particular embodiments, a stored WHR measurement may be used if it is not too stale, i.e., if it has been created with a predetermined length of time.

In step 1320, the system may determine one or more stress-related parameters. In particular embodiments, the stress-related parameters may be determined by measuring those parameters based on output from a heart-rate sensor and/or an accelerometer of the user's client device. In particular embodiments, stress-related parameters may be accessed from a data store. In particular embodiments, the system may record measured stress-related parameters (e.g., a start time of stress, a start time of stress resilience) in a data store of the system.

In step 1330, the system may determine correlations between the WHR of the user and the stress-related parameters, whether by empirically determining such correlations or by estimating such correlations based on suitable data. In particular embodiments, the correlations between the WHR and the stress-related parameters may be determined based on the data from a period of time, for example, a period of multiple days (e.g., 5 days to 7 days), one or more weeks, or one or more months. In particular embodiments, the system may determine correlations between the stress-related parameters and the parameters related to a waist-hip measurement using an artificial intelligence (AI) and machine learning (ML) algorithm. In particular embodiments, the correlations between a waist-hip measurement and the stress-related parameters may include an increase in WHR leading to a decrease in stress resilience, or vice versa. In particular embodiments, the correlations between a waist-hip measurement and the stress-related parameters may include an increase in waist size leading to a decrease in stress resilience. In particular embodiments, the correlations between the waist-hip measurement and the stress-related parameters may include an increase in WHR or waist size leading to an increase in the number of acute stress episodes. In particular embodiments, the correlations between the waist-hip measurement and the stress-related parameters may include a high stress level over a period of time leading to an increase in WHR or an increase in waist size. In particular embodiments, the correlations between the waist-hip measurement and the stress-related parameters may include a decrease in the stress resilience leading to an increase in WHR or an increase in waist size.

In particular embodiments, the system may monitor stress-related parameters (e.g., stress resilience) and LPHA axis activation to determine changes over time and the correlations between those changes. In particular embodiments, the system may monitor changes in WHR in the context of changes in stress management and diet management. As described more fully below, in step 1340 the system may provide feedback to the user based on the determined correlations between the stress-related parameters and the WHR of the user. Although this disclosure describes and illustrates particular steps of the method of FIG. 13 as occurring in a particular order, this disclosure contemplates any suitable steps of the method of FIG. 13 occurring in any suitable order. Moreover, although this disclosure describes and illustrates an example method for determining correlations between WHR or waist-size and stress-related parameters and providing feedback to the user based on the correlations including the particular steps of the method of FIG. 13, this disclosure contemplates any suitable method for determining correlations between WHR or waist size and stress-related parameters and providing feedback to the user based on the correlations including any suitable steps, which may include all, some, or none of the steps of the method of FIG. 13, where appropriate. Furthermore, although this disclosure describes and illustrates particular components, devices, or systems carrying out particular steps of the method of FIG. 13, this disclosure contemplates any suitable combination of any suitable components, devices, or systems carrying out any suitable steps of the method of FIG. 13.

Figure 14:
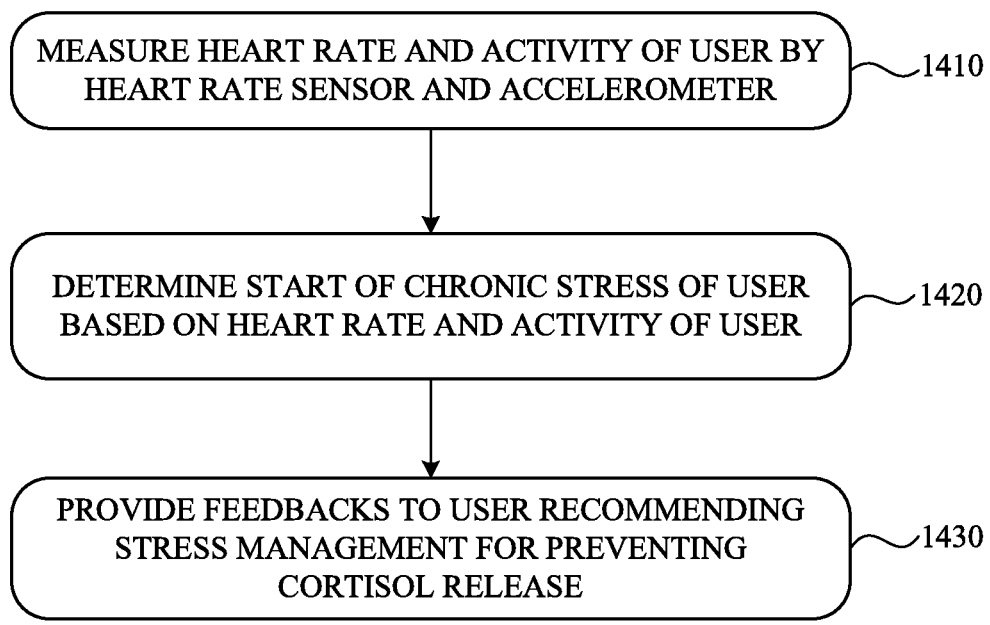
FIG. 14 illustrates an example method for determining a start of chronic stress and providing feedback to the user for preventing cortisol release.

FIG. 14 illustrates an example method for determining a start of an episode of chronic stress and providing feedback to the user for preventing cortisol release. In step 1410, the system may measure the heart rate and activity of the user using, e.g, a heart rate sensor and an accelerometer of the usre's client device. The heart rate level may be used as an indicator of stress level, as illustrated in FIG. 6. In particular embodiments, the system may determine or access a waist-hip measurement including, for example, a waist size, a hip size, a WHR and may record the waist-hip measurement in the context of the heart rate and user activity in a data store of the system. In step 1420, the system may detect a chronic stress episode and determine the start of the chronic stress based at least on the heart rate of the user. In particular embodiments, the chronic stress may be indicated by the heart rate increasing over time and exceeding the maximum resting heart rate of the user. In particular embodiments, the start of chronic stress may be indicated by the heart rate starting to increase. In particular embodiments, the system may determine a number of stress-related parameters based on the heart rate and the activity of the user. For example, as described above, the system may differentiate between chronic and acute stress. In particular embodiments, the system may determine and store tahe waist-hip measurement in context of the stress-related parameters. Chronic stress may lead to the LHPA axis activation and cortisol release which may increase belly fat in the user. In step 1430, the system may provide feedback to the user recommending stress-management techniques for preventing cortisol release, such as the stress-management techniques described below. Although this disclosure describes and illustrates particular steps of the method of FIG. 14 as occurring in a particular order, this disclosure contemplates any suitable steps of the method of FIG. 14 occurring in any suitable order. Moreover, although this disclosure describes and illustrates an example method for determining a start of chronic stress and providing feedback to the user for preventing cortisol release including the particular steps of the method of FIG. 14, this disclosure contemplates any suitable method for determining a start of chronic stress and providing feedback to the user for preventing cortisol release including any suitable steps, which may include all, some, or none of the steps of the method of FIG. 14, where appropriate. Furthermore, although this disclosure describes and illustrates particular components, devices, or systems carrying out particular steps of the method of FIG. 14, this disclosure contemplates any suitable combination of any suitable components, devices, or systems carrying out any suitable steps of the method of FIG. 14.

Figure 15:
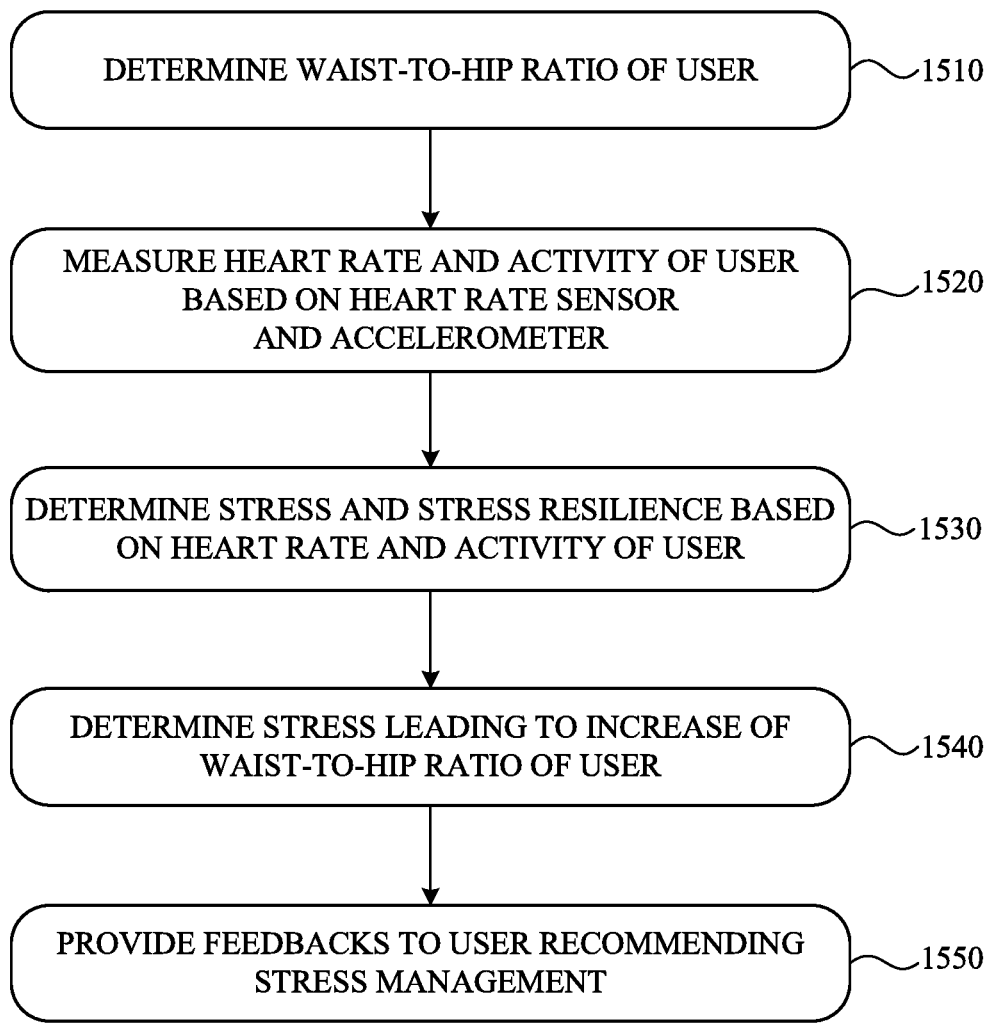
FIG. 15 illustrates an example method for determining high stress leading to an increase of the WHR of a user and providing feedback to the user for stress management.

FIG. 15 illustrates an example method for determining high stress leading to an increase of the WHR of a user and providing feedback to the user for stress management. In step 1510, the system may determine or access the WHR of the user. In particular embodiments, the system may determine the WHR of the user and record the WHR in thae data store of the system for a period of time, for example, a period of multiple days, a period of one or more weeks, or a period of one or more months. In step 1520, the system may measure the heart rate and activity of the user based on, e.g., output from a heart rate sensor and an accelerometer. In step 1530, the system may determine the chronic stress and the stress resilience of the user based on, e.g., the heart rate and activity of the user. In particular embodiments, the systems may also determine other stress-related parameters, for example, a stress level or a period of chronic stress. In particular embodiments, the system may determine a high stress level associated with an episode of chronic stress. In step 1540, the system may determine that chronic stress (e.g., a chronic stress with a high stress level) has led to an increase of the WHR of the user. In particular embodiments, the correlation of chronic stress leading to increase of the WHR may be determined based on data from a period of time, for example, but not limited to, a period from several days to weeks. In particular embodiments, the correlation of chronic stress leading to the increase of the WHR may be determined based on data of a number of measurements, for example, but not limited to, 30 measurements, 50 measurements, 100 measurements, or any reasonable number of measurements. In step 1550, the system may provide feedback to the user recommending stress management techniques. Although this disclosure describes and illustrates particular steps of the method of FIG. 15 as occurring in a particular order, this disclosure contemplates any suitable steps of the method of FIG. 15 occurring in any suitable order. Moreover, although this disclosure describes and illustrates an example method for determining high stress leading to an increase of the WHR of a user and providing feedback to the user for stress management including the particular steps of the method of FIG. 15, this disclosure contemplates any suitable method for determining high stress leading to an increase of the WHR of a user and providing feedback to the user for stress management including any suitable steps, which may include all, some, or none of the steps of the method of FIG. 15, where appropriate. Furthermore, although this disclosure describes and illustrates particular components, devices, or systems carrying out particular steps of the method of FIG. 15, this disclosure contemplates any suitable combination of any suitable components, devices, or systems carrying out any suitable steps of the method of FIG. 15.

Figure 16:
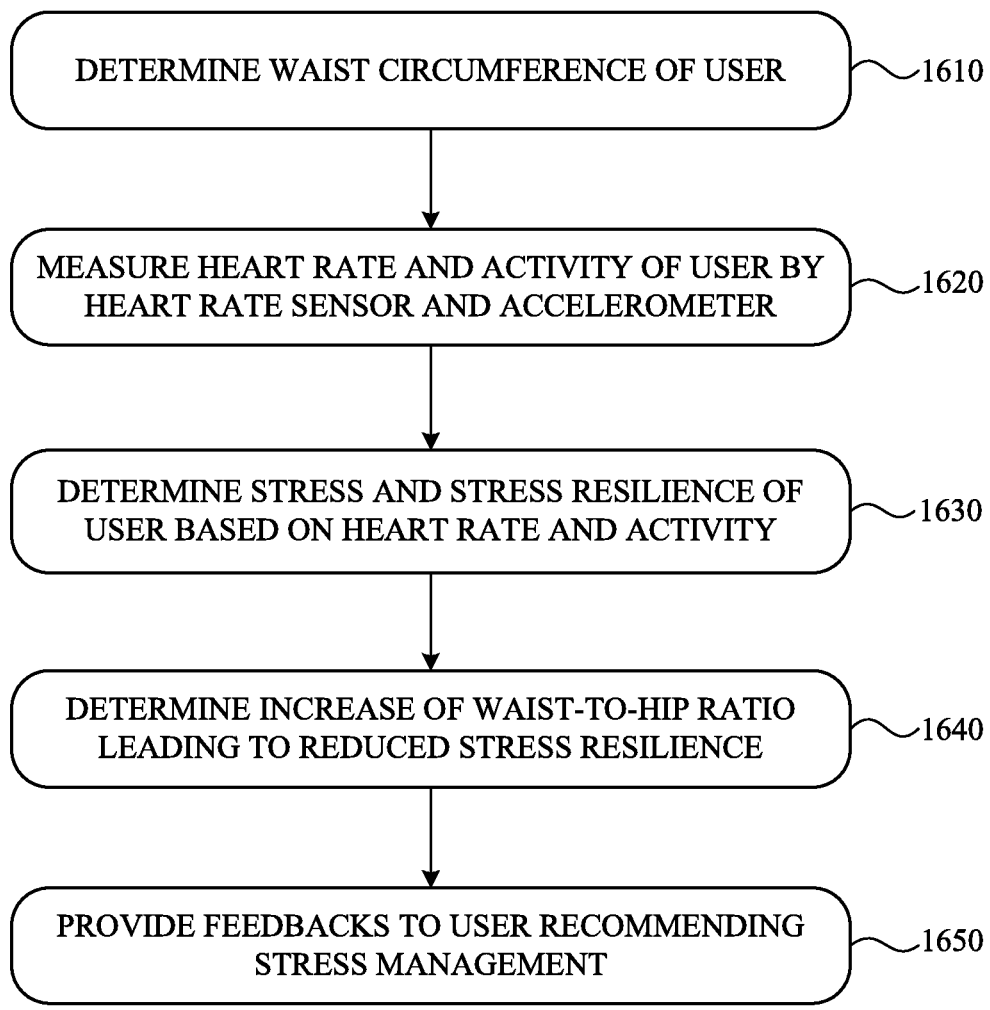
FIG. 16 illustrates an example method for determining an increase of the WHR of a user leading to reduced stress resilience of the user and providing feedback to the user for stress management.

FIG. 16 illustrates an example method for determining an increase of the WHR of a user leading to reduced stress resilience of the user and providing feedback to the user for stress management. In step 1610, the system may determine the WHR of the user. In particular embodiments, the system may determine the WHR of the user for a period of time and may record the WHR in a data store of the system. In step 1620, the system may measure the heart rate and activity of the user based on, e.g., output from a heart-rate sensor and an accelerometer of the client device. In particular embodiments, the system may record the measured heart rate and activity of the user over time in a data store of the system.

In step 1630, the system may determine episodes of chronic stress and the stress resilience of the user based on the measured heart rate and activity of the user. In particular embodiments, the stress resilience may be measured or gauged by a recovering time period of the user or a recovering speed of the user from the stress. In step 1640, the system may determine an increase in the WHR of the user leading to reduced stress resilience of the user. In particular embodiments, the system may determine the correlations between the WHR and the stress resilience of the user based on data over a period of time, for example, from several days to weeks. In step 1650, the system may provide feedback to the user recommending stress management techniques. Although this disclosure describes and illustrates particular steps of the method of FIG. 16 as occurring in a particular order, this disclosure contemplates any suitable steps of the method of FIG. 16 occurring in any suitable order. Moreover, although this disclosure describes and illustrates an example method for determining an increase of the WHR of a user leading to reduced stress resilience of the user and providing feedback to the user for stress management including the particular steps of the method of FIG. 16, this disclosure contemplates any suitable method for determining an increase of the WHR of a user leading to reduced stress resilience of the user and providing feedback to the user for stress management including any suitable steps, which may include all, some, or none of the steps of the method of FIG. 16, where appropriate. Furthermore, although this disclosure describes and illustrates particular components, devices, or systems carrying out particular steps of the method of FIG. 16, this disclosure contemplates any suitable combination of any suitable components, devices, or systems carrying out any suitable steps of the method of FIG. 16.

In particular embodiments, the system may provide the feedback to the user through one or more client systems, for example, a mobile device or a wearable device. In particular embodiments, the feedback to user may be displayed on one or more screens of the client system. In particular embodiments, the feedback may include elements describing or illustrating the feedback, for example, but not limited to, text, icons, graphics, voices, vibrations, or any combination of these elements. In particular embodiments, the feedback may be delivered to the user through one or more user interfaces or devices, for example, but not limited to, a display screen, a speaker, a vibrating engine, a touchable device, or any combination of the user interfaces and devices.

In particular embodiment, the feedback to user may include suggestions for the user to immediately reduce the user's stress level, for example by recommending the user engage in one or more stress management techniques, such as but not limited to a recommendation for a relaxing activity, a recommendation for an exercise activity, a recommendation that the user engage in deep breathing, a recommendation for a progressive muscle relaxation, a recommendation that the user engage in mindful meditation, a recommendation that the user engage in yoga, a recommendation that the user engage in Tai chi, or a recommendation that the user self-massage. In particular embodiments, feedback may include a lifestyle recommendation, such as a diet or excise recommendation. For example, the feedback may include a recommendation for a diet change, such as a recommendation that the user have a more carbohydrate-rich diet, when the system determines that the user's stress is correlated with an increase in WHR over time. In particular embodiments, a recommendation may include a description of a body shape profile, a risk profile, and/or one or more stress-related parameters.

Figure 17:
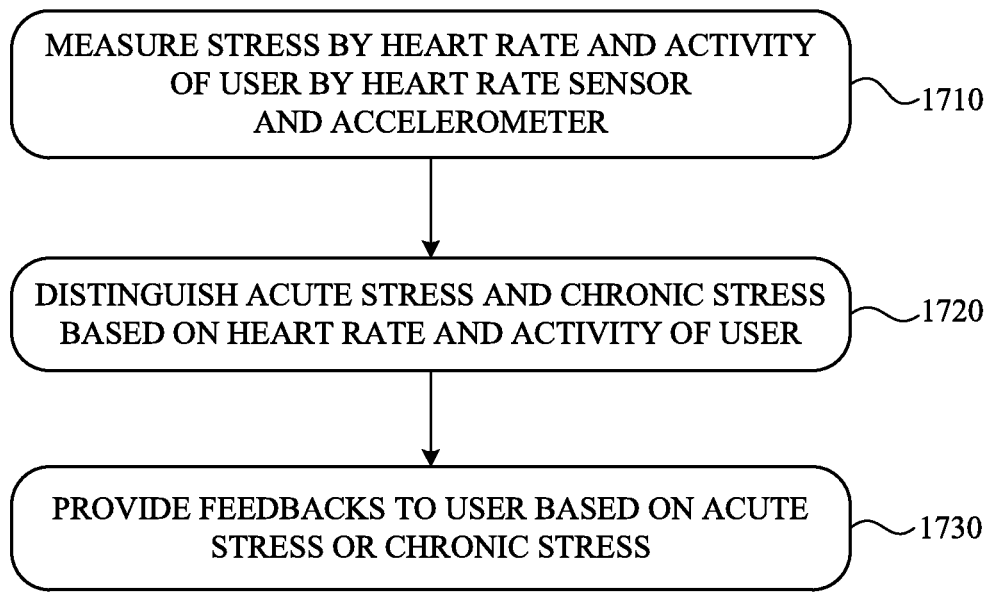
FIG. 17 illustrates an example method for distinguishing acute stress and chronic stress based on a user's heart rate and activity and providing feedback to the user based on the type of stress the user is experiencing.

FIG. 17 illustrates an example method for distinguishing acute stress and chronic stress based on a user's heart rate and activity and providing feedback to the user based on the type of stress the user is experiencing. In step 1710, the system may measure the user's stress by measuring the heart rate and activity of the user based on, e.g., output from a heart rate sensors and an accelerometer in the client device. The system may determine that the user is experiencing stress. In step 1720, the system may determine the type of stress that the user is experiencing by distinguishing acute stress and chronic stress based on the heart rate and activity of the user. In particular embodiments, the system may determine whether the measured stress is an acute stress or a chronic stress based on a length of time of the measured stress, a heart rate during the time of the measured stress, and/or an activity level of the user during the stress episode. In particular embodiments, the system may determine the measured stress is acute stress based on the characters of the measured stress including, for example, the measured stress having a short time period and a high stress level (i.e., a high heart rate). In particular embodiments, the system may determine the measured stress being a chronic stress based on the measured stress having a relatively long time period and a relatively low stress level.

In step 1730, the system may provide feedback to the user based on the determined acute stress or chronic stress. In particular embodiments, the system may provide feedback based on the determined acute stress and the feedback may include descriptions about the episode of the acute stress. In particular embodiments, the system may provide feedback based on the determined chronic stress and the feedback may include recommendations for stress management techniques. Although this disclosure describes and illustrates particular steps of the method of FIG. 17 as occurring in a particular order, this disclosure contemplates any suitable steps of the method of FIG. 17 occurring in any suitable order. Moreover, although this disclosure describes and illustrates an example method for distinguishing acute stress and chronic stress based on a user's heart rate and activity and providing feedback to the user based on the type of stress the user is experiencing including the particular steps of the method of FIG. 17, this disclosure contemplates any suitable method for distinguishing acute stress and chronic stress based on a user's heart rate and activity and providing feedback to the user based on the type of stress the user is experiencing including any suitable steps, which may include all, some, or none of the steps of the method of FIG. 17, where appropriate. Furthermore, although this disclosure describes and illustrates particular components, devices, or systems carrying out particular steps of the method of FIG. 17, this disclosure contemplates any suitable combination of any suitable components, devices, or systems carrying out any suitable steps of the method of FIG. 17.

Figure 18:
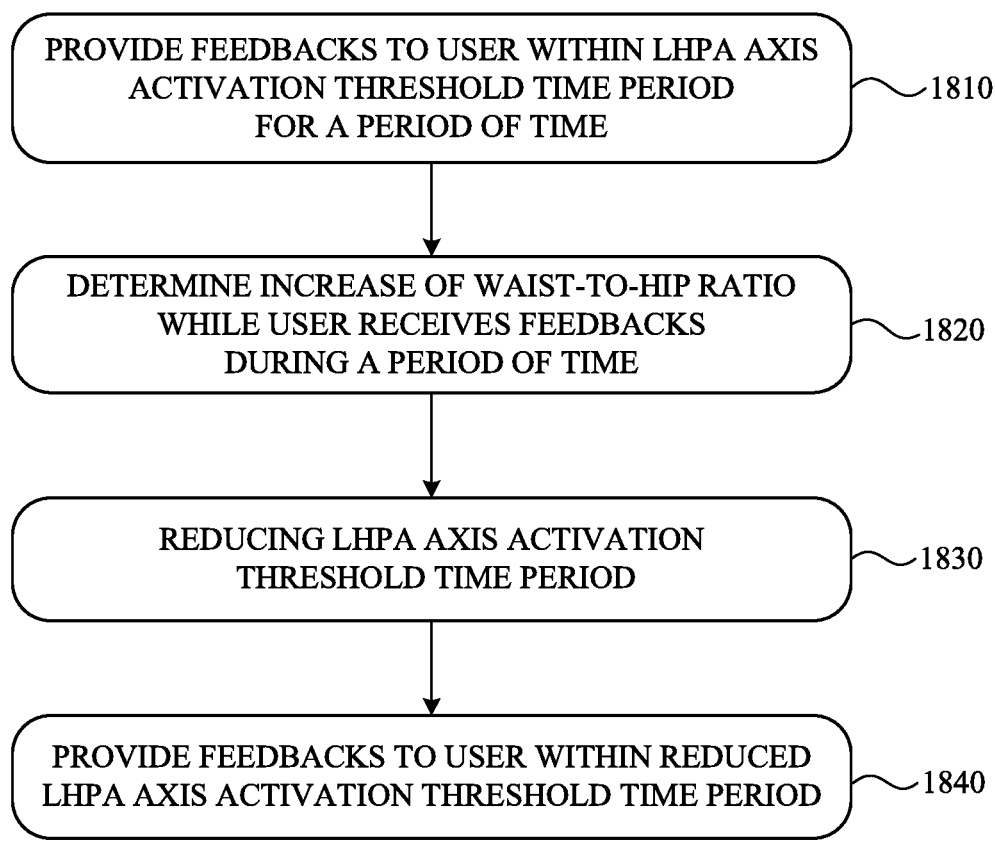
FIG. 18 illustrates an example method for providing feedback to user within an LHPA axis activation threshold time period.

FIG. 18 illustrates an example method for providing feedback to user within the reduced LHPA axis activation threshold time period. In particular embodiments, the system may provide feedback to the user within an LHPA axis activation threshold time period to prevent or reduce the cortisol release. The LHPA axis activation threshold time period may be the time period from the start of the chronic stress until the LHPA axis activation which may be associated with the cortisol release. In order to prevent the LHPA axis activation and the cortisol release, the system may need to provide feedback to the user so that the user can engage in activity to reduce the user's heart rate to a resting heart rate before LHPA axis activation and cortisol release. In step 1810, when the system detects an episode of chronic stress, the system may provide feedback to the user within the LHPA axis activation threshold time period of the user. In particular embodiments, the system may use an initial time period (e.g., 25 minutes) as the initial LHPA axis activation threshold time period. In step 1820, the system may determine an increase in the WHR (or other waist-size measurements) of the user during a period of time that the user has been receiving stress-related feedback. For example, the system may determine that, although the user has been receiving feedback throughout the course of three month to engage in stress reduction before the end of the LHPA axis activation threshold time period during an episode of chronic stress, the user's WHR has nevertheless increased during over those three months. The increase of the WHR of the user may indicate that the system is not providing timely feedback to the user in response to a chronic stress. Thus, the LHPA axis activation threshold time period associated with that user may be too long.

In step 1830, the system may reduce the LHPA axis activation threshold time period for that user to a shorter time period. In step 1840, when an episode of chronic stress is detected, the system may provide feedback to the user within the reduced LHPA axis activation threshold time period. In particular embodiments, the system may repeat the above steps to determine an accurate LHPA axis activation threshold time period for the user. In particular embodiments, the system may determine the accurate LHPA axis activation threshold time period for the user based on the measurement data for a period of time, for example, a period from days to weeks. In particular embodiments, the system may determine the accurate LHPA axis activation threshold time period based on measurement data from a number of measurements, for example, at least 100 measurements. Although this disclosure describes and illustrates particular steps of the method of FIG. 18 as occurring in a particular order, this disclosure contemplates any suitable steps of the method of FIG. 18 occurring in any suitable order. Moreover, although this disclosure describes and illustrates an example method for providing feedback to user within an LHPA axis activation threshold time period including the particular steps of the method of FIG. 18, this disclosure contemplates any suitable method for providing feedback to a user within the reduced LHPA axis activation threshold time period including any suitable steps, which may include all, some, or none of the steps of the method of FIG. 18, where appropriate. Furthermore, although this disclosure describes and illustrates particular components, devices, or systems carrying out particular steps of the method of FIG. 18, this disclosure contemplates any suitable combination of any suitable components, devices, or systems carrying out any suitable steps of the method of FIG. 18.

Figure 19:
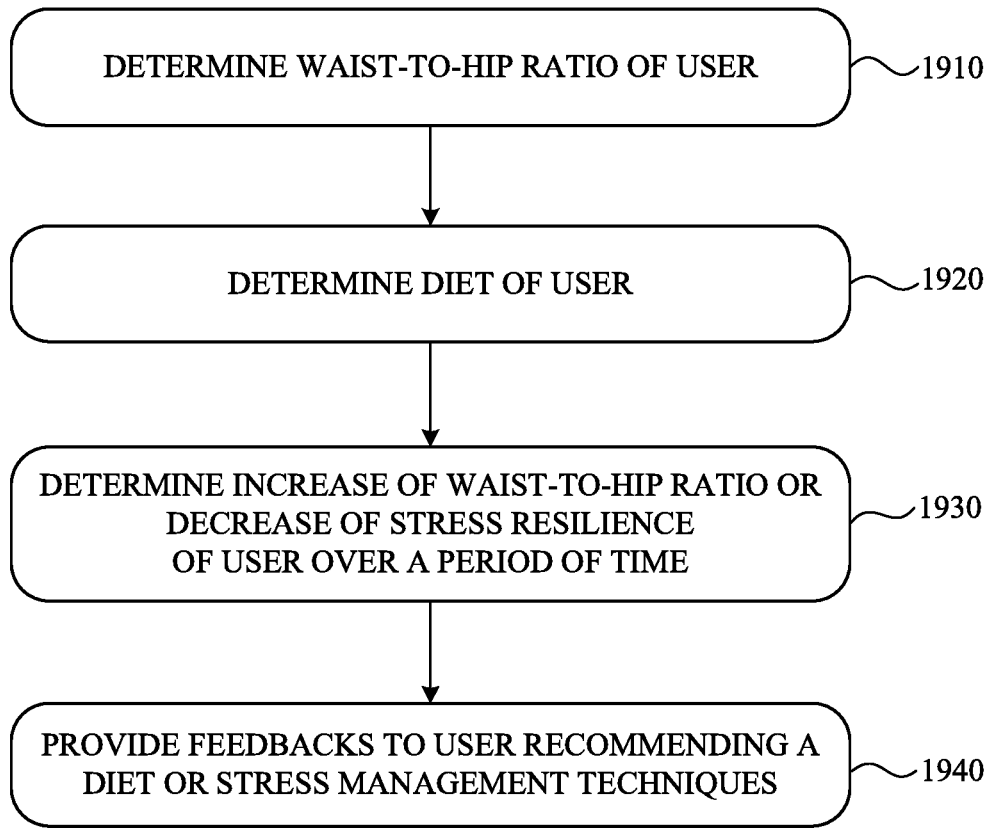
FIG. 19 illustrates an example method for determining an increase of WHR of the user and providing feedback to the user recommending a diet or stress management.

FIG. 19 illustrates an example method for determining an increase of WHR of the user and providing feedback to the user recommending a diet change or stress management technique. In step 1910, the system may determine the WHR of the user. In particular embodiments, the system may determine the WHR of the user over a period of time, for example, from days to weeks, and may record the determined WHR of the user in the data store of the system. In particular embodiments, the system may determine waist size instead of WHR. In step 1920, the system may determine the diet of the user. In particular embodiments, the system may determine the diet of the user over a period of time, for example, from days to weeks.

In particular embodiments, the system may determine the diet of the user using an artificial intelligence (AI) and machine learning (ML) algorithm. In particular embodiments, the system may determine the diet of the user by comparing the user's meals with a number of meal pictures stored in a database of the system. In particular embodiments, the system may determine the diet of the user by determining one or more of characterizations of the user's food, for example, but not limited to, a food type, a food calorie metric, a food carbohydrate content, a food protein content, or a food fat content. In particular embodiments, the system may determine a low-carbohydrate diet of the user. In particular embodiments, the system may determine the correlations between the diet of the user and stress-related parameters using, e.g., a machine-learning algorithm and a database of meal pictures.

In step 1930, the system may determine an increase of the WHR of the user or a decrease of the stress resilience of the user over a period of time, for example, from days to weeks. In particular embodiments, the system may determine the diet of the user as being one of the factors contributing to the increase of WHR of the user or the decrease of the stress resilience of the user. In particular embodiments, the system may determine that a low-carbohydrate diet of the user has led to the increase of the WHR of the user, the increase in stress in case of higher WHR, or the decrease of the stress resilience of the user. In particular embodiments, the system may determine any correlations between the diet of the user over a period of time and the stress-related parameters of the user over the same period of time.

In step 1940, the system may provide feedback to the user recommending a diet or stress management technique. In particular embodiments, the system may allow the user to take pictures of meals of the user and may provide feedback based on the type of food and calories. Although this disclosure describes and illustrates particular steps of the method of FIG. 19 as occurring in a particular order, this disclosure contemplates any suitable steps of the method of FIG. 19 occurring in any suitable order. Moreover, although this disclosure describes and illustrates an example method for determining an increase of WHR or waist size of the user and providing feedback to the user recommending a diet change or stress management including the particular steps of the method of FIG. 19, this disclosure contemplates any suitable method for determining an increase of WHR or waist size of the user and providing feedback to the user recommending a diet change or stress management including any suitable steps, which may include all, some, or none of the steps of the method of FIG. 19, where appropriate. Furthermore, although this disclosure describes and illustrates particular components, devices, or systems carrying out particular steps of the method of FIG. 19, this disclosure contemplates any suitable combination of any suitable components, devices, or systems carrying out any suitable steps of the method of FIG. 19.

Figure 20:
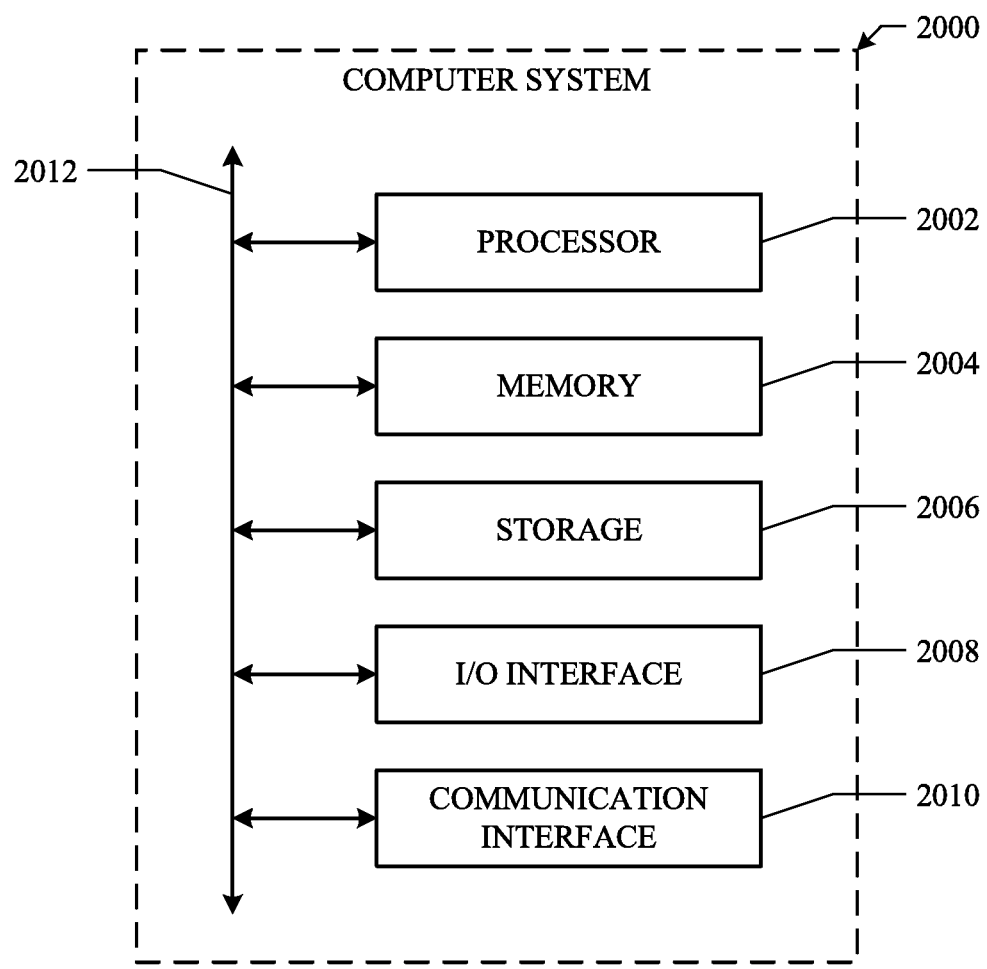
FIG. 20 illustrates an example computer system according to particular embodiments.

FIG. 20 illustrates an example computer system 2400 according to particular embodiments. In particular embodiments, one or more computer systems 2400 perform one or more steps of one or more methods described or illustrated herein. In particular embodiments, one or more computer systems 2400 provide functionality described or illustrated herein. In particular embodiments, software running on one or more computer systems 2400 performs one or more steps of one or more methods described or illustrated herein or provides functionality described or illustrated herein. Particular embodiments include one or more portions of one or more computer systems 2400. Herein, reference to a computer system may encompass a computing device, and vice versa, where appropriate. Moreover, reference to a computer system may encompass one or more computer systems, where appropriate.

This disclosure contemplates any suitable number of computer systems 2400. This disclosure contemplates computer system 2400 taking any suitable physical form. As example and not by way of limitation, computer system 2400 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 2400 may include one or more computer systems 2400; be unitary or distributed; span multiple locations; span multiple machines; span multiple data centers; or reside in a cloud, which may include one or more cloud components in one or more networks. Where appropriate, one or more computer systems 2400 may perform without substantial spatial or temporal limitation one or more steps of one or more methods described or illustrated herein. As an example and not by way of limitation, one or more computer systems 2400 may perform in real time or in batch mode one or more steps of one or more methods described or illustrated herein. One or more computer systems 2400 may perform at different times or at different locations one or more steps of one or more methods described or illustrated herein, where appropriate.

In particular embodiments, computer system 2400 includes a processor 2402, memory 2404, storage 2406, an input/output (I/O) interface 2408, a communication interface 2410, and a bus 2412. Although this disclosure describes and illustrates a particular computer system having a particular number of particular components in a particular arrangement, this disclosure contemplates any suitable computer system having any suitable number of any suitable components in any suitable arrangement.

In particular embodiments, processor 2402 includes hardware for executing instructions, such as those making up a computer program. In particular embodiments, the computer program causes the processor 2402 to perform one or more steps of one or more methods described or illustrated herein or provides functionality described or illustrated herein. In this way, the processor 2402 coupled to the computer program is a special purpose processor for performing the functions defined by the computer program. As an example and not by way of limitation, to execute instructions, processor 2402 may retrieve (or fetch) the instructions from an internal register, an internal cache, memory 2404, or storage 2406; decode and execute them; and then write one or more results to an internal register, an internal cache, memory 2404, or storage 2406. In particular embodiments, processor 2402 may include one or more internal caches for data, instructions, or addresses. This disclosure contemplates processor 2402 including any suitable number of any suitable internal caches, where appropriate. As an example and not by way of limitation, processor 2402 may include one or more instruction caches, one or more data caches, and one or more translation lookaside buffers (TLBs). Instructions in the instruction caches may be copies of instructions in memory 2404 or storage 2406, and the instruction caches may speed up retrieval of those instructions by processor 2402. Data in the data caches may be copies of data in memory 2404 or storage 2406 for instructions executing at processor 2402 to operate on; the results of previous instructions executed at processor 2402 for access by subsequent instructions executing at processor 2402 or for writing to memory 2404 or storage 2406; or other suitable data. The data caches may speed up read or write operations by processor 2402. The TLBs may speed up virtual-address translation for processor 2402. In particular embodiments, processor 2402 may include one or more internal registers for data, instructions, or addresses. This disclosure contemplates processor 2402 including any suitable number of any suitable internal registers, where appropriate. Where appropriate, processor 2402 may include one or more arithmetic logic units (ALUs); be a multi-core processor; or include one or more processors 2402. Although this disclosure describes and illustrates a particular processor, this disclosure contemplates any suitable processor.

In particular embodiments, memory 2404 includes main memory for storing instructions for processor 2402 to execute or data for processor 2402 to operate on. As an example and not by way of limitation, computer system 2400 may load instructions from storage 2406 or another source (such as, for example, another computer system 2400) to memory 2404. Processor 2402 may then load the instructions from memory 2404 to an internal register or internal cache. To execute the instructions, processor 2402 may retrieve the instructions from the internal register or internal cache and decode them. During or after execution of the instructions, processor 2402 may write one or more results (which may be intermediate or final results) to the internal register or internal cache. Processor 2402 may then write one or more of those results to memory 2404. In particular embodiments, processor 2402 executes only instructions in one or more internal registers or internal caches or in memory 2404 (as opposed to storage 2406 or elsewhere) and operates only on data in one or more internal registers or internal caches or in memory 2404 (as opposed to storage 2406 or elsewhere). One or more memory buses (which may each include an address bus and a data bus) may couple processor 2402 to memory 2404. Bus 2412 may include one or more memory buses, as described below. In particular embodiments, one or more memory management units (MMUs) reside between processor 2402 and memory 2404 and facilitate accesses to memory 2404 requested by processor 2402. In particular embodiments, memory 2404 includes random access memory (RAM). This RAM may be volatile memory, or may be dynamic RAM (DRAM) or static RAM (SRAM). Moreover, where appropriate, this RAM may be single-ported or multi-ported RAM. This disclosure contemplates any suitable RAM. Memory 2404 may include one or more memories 2404, where appropriate. Although this disclosure describes and illustrates particular memory, this disclosure contemplates any suitable memory.

In particular embodiments, storage 2406 includes mass storage for data or instructions. As an example and not by way of limitation, storage 2406 may include a hard disk drive (HDD), a floppy disk drive, flash memory, an optical disc, a magneto-optical disc, magnetic tape, or a Universal Serial Bus (USB) drive or a combination of two or more of these. Storage 2406 may include removable or non-removable (or fixed) media, where appropriate. Storage 2406 may be internal or external to computer system 2400, where appropriate. In particular embodiments, storage 2406 is non-volatile, solid-state memory. In particular embodiments, storage 2406 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 2406 taking any suitable physical form. Storage 2406 may include one or more storage control units facilitating communication between processor 2402 and storage 2406, where appropriate. Where appropriate, storage 2406 may include one or more storages 2406. Although this disclosure describes and illustrates particular storage, this disclosure contemplates any suitable storage.

In particular embodiments, I/O interface 2408 includes hardware, software, or both, providing one or more interfaces for communication between computer system 2400 and one or more I/O devices. Computer system 2400 may include one or more of these I/O devices, where appropriate. One or more of these I/O devices may enable communication between a person and computer system 2400. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 2408 for them. Where appropriate, I/O interface 2408 may include one or more device or software drivers enabling processor 2402 to drive one or more of these I/O devices. I/O interface 2408 may include one or more I/O interfaces 2408, where appropriate. Although this disclosure describes and illustrates a particular I/O interface, this disclosure contemplates any suitable I/O interface.

In particular embodiments, communication interface 2410 includes hardware, software, or both providing one or more interfaces for communication (such as, for example, packet-based communication) between computer system 2400 and one or more other computer systems 2400 or one or more networks. As an example and not by way of limitation, communication interface 2410 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 2410 for it. As an example and not by way of limitation, computer system 2400 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 2400 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 2400 may include any suitable communication interface 2410 for any of these networks, where appropriate. Communication interface 2410 may include one or more communication interfaces 2410, where appropriate. Although this disclosure describes and illustrates a particular communication interface, this disclosure contemplates any suitable communication interface.

In particular embodiments, bus 2412 includes hardware, software, or both coupling components of computer system 2400 to each other. As an example and not by way of limitation, bus 2412 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 2412 may include one or more buses 2412, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. A method comprising, by one or more computing devices:
   accessing, by the one or more computing devices, a waist-hip measurement of a user;
   detecting, by the one or more computing devices, a start of a stress episode during one or more of heart-rate monitoring or activity monitoring of the user;
   determining, by the one or more computing devices, one or more stress-related stages of the user based on the one or more monitored heart rate or activity;
   determining, by the one or more computing devices, one or more correlations between the waist-hip measurement and one or more stress-related parameters of the user, wherein one of the stress-related parameters comprises an LHPA (limbic-hypothalamic-pituitary-adrenal) axis activation threshold time period;
   providing, by the one or more computing devices within the LHPA axis activation threshold time period, instructions for presenting feedback to the user, wherein the feedback is based on the determined correlations between the waist-hip measurement and the one or more stress-related parameters, and wherein a type of content in the feedback is determined based on the one or more stress-related parameters; and
   monitoring, by the one or more computing devices, changes in a waist size measurement of the user in response to presenting the feedback to the user.

2. The method of claim 1, wherein accessing the waist-hip measurement of the user comprises:
   determining, by the one or more computing devices, a waist size of the user based on an image of the waist and a finger-span of the user;
   receiving, at the one or more computing devices and from the user, a hip size of the user; and
   determining, by the one or more computing devices, a waist-to-hip ratio of the user.

3. The method of claim 2, wherein the waist size is a waist circumference or a waist length, and wherein the hip size is a hip circumference or a hip length.

4. The method of claim 1, wherein accessing the waist-hip measurement of the user comprises:
   determining, by the one or more computing devices, a waist size and a hip size based on an image of the waist, the hip, and a finger-span of the user; and
   determining, by the one or more computing devices, a waist-to-hip ratio of the user.

5. The method of claim 1, wherein the one or more stress-related parameters further comprise one or more of:
   an acute stress;
   one or more acute stress episodes;
   a chronic stress;
   a period of chronic stress;
   a stress resilience;
   a period of stress resilience;
   an LHPA axis activation;
   a first heart rate during a first time period comprising at least the period of chronic stress and the period of stress resilience;
   a first stress level during the first time period;
   a first activity metric during the first time period;
   a second heart rate during a second time period comprising at least multiple days;
   a second stress level during the second time period; or
   a second activity metric during the second time period.

6. The method of claim 5, wherein:
   the LHPA axis activation threshold time period comprises a start of the period of chronic stress until the LHPA axis activation; and
   the LHPA axis activation corresponds to a cortisol release time.

7. The method of claim 5, wherein:
   the first or second heart rates are measured by an electrocardiography (ECG) sensor or a photoplethysmography (PPG) sensor in a client device.

8. The method of claim 7, wherein the client device comprises a wearable device.

9. The method of claim 5, wherein the first or second activity metrics are determined based on output from an accelerometer in a client device.

10. The method of claim 5, wherein the one or more stress-related parameters further comprises:
    determining, by the one or more computing devices, whether a measured stress is the acute stress or the chronic stress based at least on:
    a length of time of the measured stress; and
    a heart rate during the time of the measured stress.

11. The method of claim 5, wherein the period of stress resilience comprises the time period from which the user's heart rate starts decreasing during a period of stress until the heart rate of the user is within a resting heart rate.

12. The method of claim 1, wherein determining the one or more correlations between the waist-hip measurement and the one or more stress-related parameters of the user comprises:
    determining, by the one or more computing devices, a high stress over a preceding time period leading to an increase of a waist-to-hip ratio or an increase of a waist size.

13. The method of claim 1, wherein determining the one or more correlations between the waist-hip measurement and the one or more stress-related parameters of the user comprises determining, by the one or more computing devices:
    an increase in a waist-to-hip ratio or an increase in a waist size leading to a decrease in a stress resilience; or
    an increase in a number of acute stress episodes.

14. The method of claim 13, wherein the feedback comprises one or more suggestions to immediately reduce a stress level of the user.

15. The method of claim 1, wherein providing the feedback to the user based on the one or more stress-related parameters comprises providing, by the one or more computing devices, feedback after the start of an episode of chronic stress.

16. The method of claim 1, further comprising recording, by the one or more computing devices, the waist-hip measurement in association with the one or more stress-related parameters.

17. The method of claim 16, wherein the waist-hip measurement comprises at least a waist size or a waist-to-hip ratio, and wherein the one or more stress-related parameters comprises at least a stress resilience or an LHPA axis activation.

18. The method of claim 1, wherein the feedback comprises one or more of:
    a description of the one or more stress-related parameters;
    one or more stress management techniques;
    one or more acute stress episodes;
    a recommendation for a relaxing activity;
    a recommendation for an exercise activity;
    a recommendation for a deep breathing activity;

a recommendation for a progressive muscle relaxation activity;
a recommendation for a mindfulness meditation activity;
a recommendation for a body scan meditation activity;
a recommendation for a yoga activity;
a recommendation for a Tai chi activity;
a recommendation for a self-massage activity;
a recommendation for a diet change;
a body shape profile; or
a risk profile based on the body shape profile.

19. The method of claim 1, wherein the LHPA axis activation threshold time period has an initial value of 25 minutes from the start of a detected stress episode.

20. The method of claim 1, further comprising:
reducing, by the one or more computing devices, the LHPA axis activation threshold time period in response to a determination that a waist size or a waist-to-hip ratio of the user has increased.

21. The method of claim 1, further comprising:
determining, by the one or more computing devices, a body shape of the user using a contour detection and a shape matching, wherein the feedback comprises a risk profile based on the body shape of the user.

22. The method of claim 1, further comprising:
determining, by the one or more computing devices, a diet of the user; and
determining, by the one or more computing devices, an increase in a waist-to-hip ratio or a decrease in a stress resilience of the user, wherein the feedback comprises a diet recommendation or a stress-management-technique recommendation.

23. The method of claim 22, wherein determining the diet of the user comprises: determining, by a machine learning algorithm and based on one or more meal pictures in a database, one or more of:
a food type;
a food calorie metric;
a food carbohydrate content;
a food protein content; or
a food fat content.

24. The method of claim 22, further comprising:
determining, by the one or more computing devices, a low-carbohydrate diet of the user; and
determining, by the one or more computing devices, an increase in a waist-to-hip ratio or an amount of stress of the user, wherein the feedback comprises a recommendation to eat less low-carbohydrate diet.

25. The method of claim 1, wherein the one or more stress-related parameters or the correlations between the waist-hip measurement and the one or more stress-related parameters are determined using a machine learning algorithm.

26. One or more computer-readable non-transitory storage media embodying software that is operable when executed to:
access a waist-hip measurement of a user;
detect a start of a stress episode during one or more of heart-rate monitoring or activity monitoring of the user;
determine one or more stress-related stages of the user based on the one or more monitored heart rate or activity;
determine one or more correlations between the waist-hip measurement and one or more stress-related parameters of the user, wherein one of the stress-related parameters comprises an LHPA (limbic-hypothalamic-pituitary-adrenal) axis activation threshold time period;
provide instructions for presenting feedback to the user within the LHPA axis activation threshold time period, wherein the feedback is based on the determined correlations between the waist-hip measurement and the one or more stress-related parameters, and wherein a type of content in the feedback is determined based on the one or more stress-related parameters; and
monitor, by the one or more computing devices, changes in a waist size measurement of the user in response to presenting the feedback to the user.

27. The media of claim 26, wherein the media further embodies software that is operable when executed to:
determine a waist size of the user based on an image of the waist and a finger-span of the user;
receive, from the user, a hip size of the user; and
determine a waist-to-hip ratio of the user.

28. The media of claim 27, wherein the waist size is a waist circumference or a waist length, and wherein the hip size is a hip circumference or a hip length.

29. The media of claim 26, wherein accessing the waist-hip measurement of the user comprises:
determining a waist size and a hip size based on an image of the waist, the hip, and a finger-span of the user; and
determining a waist-to-hip ratio of the user.

30. The media of claim 26, wherein the one or more stress-related parameters further comprise one or more of:
an acute stress;
one or more acute stress episodes;
a chronic stress;
a period of chronic stress;
a stress resilience;
a period of stress resilience;
an LHPA axis activation;
a first heart rate during a first time period comprising at least the period of chronic stress and the period of stress resilience;
a first stress level during the first time period;
a first activity metric during the first time period;
a second heart rate during a second time period comprising at least multiple days;
a second stress level during the second time period; or
a second activity metric during the second time period.

31. The media of claim 30, wherein:
the LHPA axis activation threshold time period comprises a start of the period of chronic stress until the LHPA axis activation; and
the LHPA axis activation corresponds to a cortisol release time.

32. The media of claim 30, wherein:
the first or second heart rates are measured by an electrocardiography (ECG) sensor or a photoplethysmography (PPG) sensor in a client device.

33. The media of claim 32, wherein the client device comprises a wearable device.

34. The media of claim 30, wherein the first or second activity metrics are determined based on output from an accelerometer in a client device.

35. The media of claim 30, wherein the one or more stress-related parameters further comprises:
a determination of whether a measured stress is the acute stress or the chronic stress based at least on:
a length of time of the measured stress; and
a heart rate during the time of the measured stress.

36. A system comprising:
one or more processors;
one or more cameras;
one or more sensors; and
a non-transitory memory coupled to the processors comprising instructions executable by the processors, the processors operable when executing the instructions to:
access a waist-hip measurement of a user;
detect a start of a stress episode during one or more of heart-rate monitoring or activity monitoring of the user;
determine one or more stress-related stages of the user based on the one or more monitored heart rate or activity;
determine one or more correlations between the waist-hip measurement and one or more stress-related parameters of the user, wherein one of the stress-related parameters comprises an LHPA (limbic-hypothalamic-pituitary-adrenal) axis activation threshold time period;
provide instructions for presenting feedback to the user within the LHPA axis activation threshold time period, wherein the feedback is based on the determined correlations between the waist-hip measurement and the one or more stress-related parameters, and wherein a type of content in the feedback is determined based on the one or more stress-related parameters; and
monitor, by the one or more computing devices, changes in a waist size measurement of the user in response to presenting the feedback to the user.

37. The system of claim 36, wherein the processors are further operable when executing the instructions to:
determine a waist size of the user based on an image of the waist and a finger-span of the user;
receive, from the user, a hip size of the user; and
determine a waist-to-hip ratio of the user.

38. The system of claim 37, wherein the waist size is a waist circumference or a waist length, and wherein the hip size is a hip circumference or a hip length.

39. The system of claim 36, wherein accessing the waist-hip measurement of the user comprises:
determining a waist size and a hip size based on an image of the waist, the hip, and a finger-span of the user; and
determining a waist-to-hip ratio of the user.

40. The system of claim 36, wherein the one or more stress-related parameters further comprise one or more of:
an acute stress;
one or more acute stress episodes;
a chronic stress;
a period of chronic stress;
a stress resilience;
a period of stress resilience;
an LHPA axis activation;
a first heart rate during a first time period comprising at least the period of chronic stress and the period of stress resilience;
a first stress level during the first time period;
a first activity metric during the first time period;
a second heart rate during a second time period comprising at least multiple days;
a second stress level during the second time period; or
a second activity metric during the second time period.

41. The system of claim 40, wherein:
the LHPA axis activation threshold time period comprises a start of the period of chronic stress until the LHPA axis activation; and
the LHPA axis activation corresponds to a cortisol release time.

42. The system of claim 40, wherein:
the first or second heart rates are measured by an electrocardiography (ECG) sensor or a photoplethysmography (PPG) sensor in a client device.

43. The system of claim 42, wherein the client device comprises a wearable device.

44. The system of claim 40, wherein the first or second activity metrics are determined based on output from an accelerometer in a client device.

* * * * *